United States Patent [19]

Miyazaki et al.

[11] 4,229,466
[45] Oct. 21, 1980

[54] SESQUITERPENE DERIVATIVES HAVING ANTI-COMPLEMENTARY ACTIVITY

[75] Inventors: Wasei Miyazaki; Hirotsugu Kaise; Yoshimasa Nakano; Taketoshi Izawa; Yasuo Oshiro, all of Tokushima; Masanao Shinohara, Naruto, all of Japan

[73] Assignee: Otsuka Pharmaceutical Co., Ltd., Tokyo, Japan

[21] Appl. No.: 906,300

[22] Filed: May 15, 1978

[30] Foreign Application Priority Data

Jun. 30, 1977 [JP] Japan .................. 52-78641
Dec. 29, 1977 [JP] Japan .................. 52-158959
Feb. 10, 1978 [JP] Japan .................. 53-14674

[51] Int. Cl.³ ............... A61K 31/335; C07D 307/77; C07D 307/92; A61K 31/34
[52] U.S. Cl. ................ 424/279; 260/340.5 R; 260/343.3 R; 260/346.71; 424/282; 424/285; 435/126
[58] Field of Search ............ 424/285, 279; 260/346.71, 346.22

[56] References Cited
U.S. PATENT DOCUMENTS 3,985,896  10/1976  Brenner et al. .......... 424/285
4,046,805  9/1977   Bernstein et al. ........ 424/315

Primary Examiner—Leonard Schenkman
Attorney, Agent, or Firm—Sughrue, Rothwell, Mion, Zinn and Macpeak

[57] ABSTRACT

A sesquiterpene derivative expressed by the general formula (I):

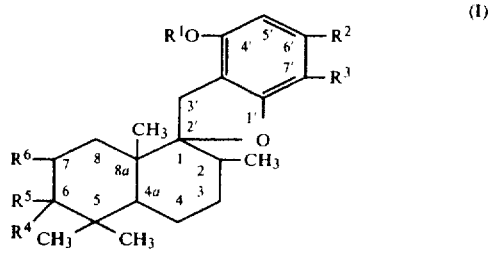

wherein $R^1$ represents a hydrogen atom, a lower alkyl group or a lower alkanoyl group; $R^2$ and $R^3$, which may be the same or different, each represents a formyl group, a hydroxymethyl group, a hydroxyl group, a carboxyl group, a lower alkanoyloxymethyl group, or a group of the formula $-CH=CR^7R^8$, wherein $R^7$ and $R^8$, which may be the same or different, each represents a hydrogen atom, a cyano group, a lower alkoxycarbonyl group or a carboxyl group, or $R^2$ and $R^3$ may combine to form a lactone ring of the formula

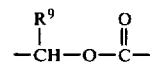

in which $R^9$ represents a hydrogen atom or a hydroxyl group; $R^4$ and $R^6$, which may be the same or different, each represents a hydroxyl group or a lower alkanoyloxy group; $R^5$ represents a hydrogen atom; $R^4$ and $R^5$ may together form an oxo group (=O); and $R^4$ and $R^6$ may combine to form a lower alkylidenedioxy group, the pharmaceutically acceptable salts thereof, processes for the production of the compounds of the general formula (I) and the salts thereof, pharmaceutical composition containing the compounds of the general formula (I) and the salts thereof, and method of use of the compounds of the general formula (I) and the salts thereof.

6 Claims, 9 Drawing Figures

SESQUITERPENE DERIVATIVES HAVING ANTI-COMPLEMENTARY ACTIVITY

BACKGROUND OF THE INVENTION

1. Field of the Invention

This invention relates to sesquiterpene derivatives, and the pharmaceutically acceptable salts thereof, which have an inhibitory activity against the complement system of animals (an anticomplementary activity) and are useful as active ingredients in therapeutic compositions effective against autoimmune diseases, nephritis, rheumatism, collagen diseases, allergic diseases, etc., or as intermediates for producing such active ingredients.

2. Description of the Prior Art

The term "complement" refers to a complex group of proteins in body fluids that, working together with antibodies or other factors, play an important role as mediators of immune, allergic, immunochemical, and/or immunopathological reactions. Reactions in which a complement participates take place in blood serum or in other body fluids and hence are considered to be humoral reactions.

It has been reported that the complement system has been shown to be involved with inflammation, coagulation, fibrinolysis, antibody-antigen reactions and other metabolic processes (cf. U.S. Pat. No. 4,021,544, Bull. World Health Org., 39 935–938 (1968), *Scientific American*, 929 (No. 5) 54–66 (1973), *Medical World News*, October 11, 53–58, 64–66 (1974), *Harvey Lectures*, 66 75–104 (1972), *The New England Journal of Medicine*, 287 489–495, 545–549, 592–596, 642–646 (1972), *The Johns Hopkins Med. J.*, 128 57–74 (1971), and *Federation Proceedings*, 32 134–137 (1973)).

Various compounds are known as compounds having an anticomplementary activity such as ethylenediamine tetraacetic acid (EDTA), Saldox, phlorizin (as described in Borsos. *J. Immunol.* 94 (4), 629 (1964)), hydroxybenzene derivatives (as described in Shir Mayer, *Biochemistry N.Y.*, 7, 3003 (1968), guanidines and phenoxyacetamides (as disclosed in B. R. Baker, *J. Med. Chem.*, 12, 408 (1968)), phosphonate esters (as disclosed in E. L. Becker, *B.B.A.*, 147, 289 (1967)), chlorophyllin, glycyrrhizin, etc. However, these compounds are not satisfactory for practical purposes because they are highly toxic or they have a low anticomplementary activity. As far as is presently known, no anticomplementary compound or agent is commercially available.

SUMMARY OF THE INVENTION

Therefore, an object of the present invention is to provide novel sesquiterpene derivatives and the salts thereof which have a high anticomplementary activity and a low toxicity.

Another object of the present invention is to provide a method for preparing sesquiterpene derivatives and the salts thereof which have a high anticomplementary activity and a low toxicity.

Yet another object of the present invention is to provide pharmaceutical compositions comprising such sesquiterpene derivatives or the salts thereof.

Still another object of the present invention is to provide a method for treating nephritis using such sesquiterpene derivatives or the salts thereof.

The present invention provides novel sesquiterpene derivatives expressed by the following general formula (I):

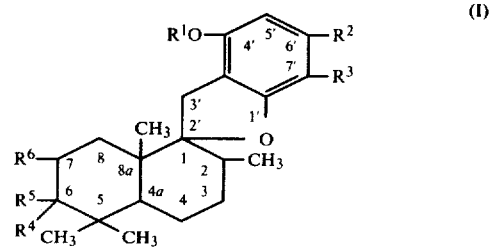

wherein $R^1$ represents a hydrogen atom, a lower alkyl group or a lower alkanoyl group; $R^2$ and $R^3$, which may be the same or different, each represents a formyl group, a hydroxymethyl group, a hydroxyl group, a carboxyl group, a lower alkanoyloxymethyl group, or a group of the formula $-CH=CR^7R^8$, wherein $R^7$ and $R^8$, which may be the same or different, each represents a hydrogen atom, a cyano group, a lower alkoxycarbonyl group or a carboxyl group, or $R^2$ and $R^3$ may combine to form a lactone ring of the formula

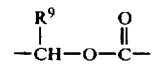

in which $R^9$ represents a hydrogen atom or a hydroxyl group; $R^4$ and $R^6$, which may be the same or different, each represents a hydroxyl group or a lower alkanoyloxy group; $R^5$ represents a hydrogen atom; $R^4$ and $R^5$ may together form an oxo group ($=O$); and $R^4$ and $R^6$ may combine to form a lower alkylidenedioxy group.

The present invention also provides pharmaceutically acceptable salts of the sesquiterpene derivatives of the general formula (I) above which are obtained by reacting the sesquiterpene derivatives of the general formula (I) with appropriate basic compounds.

The present invention also provides processes for the production of the sesquiterpene derivatives of the general formula (I) above as described in detail hereinafter utilizing as a starting material a compound of the general formula (Ia) described hereinafter.

The present invention also provides pharmaceutical compositions containing a therapeutically effective amount of the sesquiterpene derivatives of the general formula (I) above or the pharmaceutically acceptable salts thereof for achieving anticomplementary activity in animals and a method of use, particularly treating nephritic disorders in animals, comprising administering the pharmaceutical composition to a patient afflicted with such a disorder.

BRIEF DESCRIPTION OF THE ACCOMPANYING DRAWINGS

DETAILED DESCRIPTION OF THE INVENTION

I. COMPOUNDS

Figure 2:
FIGS. 1 and 2 are microphotographs of *Stachybotrys complementi* nov sp. K-76 having the ability to produce the compound of the formula (Ia) of this invention.

The sesquiterpene derivatives of the general formula (I) in accordance with this invention are described more specifically below.

The lower alkyl group represented by $R^1$ includes linear or branched alkyl groups having 1 to 4 carbon atoms such as methyl, ethyl, n-propyl, isopropyl, n-butyl, and tert-butyl.

The lower alkanoyl group represented by $R^1$ includes linear or branched alkanoyl groups having 2 to 4 carbon atoms such as acetyl, propionyl, butyryl and isobutyryl.

The lower alkanoyloxymethyl group represented by $R^2$ and $R^3$ include oxymethyl groups substituted with the above-described lower alkanoyl groups, such as acetyloxymethyl, propionyloxymethyl, butyryloxymethyl, and isobutyryloxymethyl.

The lower alkoxycarbonyl groups represented by $R^7$ and $R^8$ includes linear or branched alkoxycarbonyl groups having 2 to 5 total carbon atoms such as methoxycarbonyl, ethoxycarbonyl, n-propoxycarbonyl, n-butoxycarbonyl, and tert-butoxycarbonyl.

The lower alkanoyloxy group represented by $R^4$ and $R^6$ includes linear or branched alkanoyloxy groups having 2 to 4 carbon atoms, such as acetyloxy, propionyloxy, butyryloxy, and isobutyryloxy.

The lower alkylidenedioxy group represented by $R^4$ and $R^6$ includes those linear or branched alkylidene groups having 1 to 4 carbon atoms substituted with two oxygen atoms, such as methylidenedioxy, ethylidenedioxy, isopropylidenedioxy, and butylidenedioxy.

Specific examples of the sesquiterpene derivatives of the present invention are listed below. However, the present invention is not to be construed as being limited to these specific examples.

(1) 6,7-Dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran)

(2) 6,7-Dihydroxy-2,5,5,8a-tetramethyl-1,2,3,4,4a,5,6,7,8,8a-decahydronaphthalene-1-spiro-2'-(4',6',7'-trihydroxy-2',3'-dihydrobenzofuran)

(3) 6,7-Dihydroxy-2,5,5,8a-tetramethyl-1,2,3,4,4a,5,6,7,8,8a-decahydronaphthalene-1-spiro-2'-[6',7'-di-(2,2-dicyanovinyl)-4'-hydroxy-2',3'-dihydrobenzofuran]

(4) 6,7-Dihydroxy-2,5,5,8a-tetramethyl-1,2,3,4,4a,5,6,7,8,8a-decahydronaphthalene-1-spiro-2'-[6',7'-di-(2-cyano-2-ethoxycarbonylvinyl)-4'-hydroxy-2',3'-dihydrobenzofuran]

(5) 6,7-Dihydroxy-2,5,5,8a-tetramethyl-1,2,3,4,4a,5,6,7,8,8a-decahydronaphthalene-1-spiro-2'-[6',7'-di-(2-cyano-2-isopropoxycarbonylvinyl)-4'-hydroxy-2',3'-dihydrobenzofuran]

(6) 6,7-Dihydroxy-2,5,5,8a-tetramethyl-1,2,3,4,4a,5,6,7,8,8a-decahydronaphthalene-1-spiro-2'-[6',7'-di-(2-cyano-2-carboxyvinyl)-4'-hydroxy-2',3'-dihydrobenzofuran]

(7) 6,7-Dihydroxy-2,5,5,8a-tetramethyl-1,2,3,4,4a,5,6,7,8,8a-decahydronaphthalene-1-spiro-2'-[6',7'-di-(2-carboxyvinyl)-4'-hydroxy-2',3'-dihydrobenzofuran]

(8) 6,7-Dihydroxy-2,5,5,8a-tetramethyl-1,2,3,4,4a,5,6,7,8,8a-decahydronaphthalene-1-spiro-2'-(7'-carboxy-6'-hydroxymethyl-4'-hydroxy-2',3'-dihydrobenzofuran)

(9) 6,7-Dihydroxy-2,5,5,8a-tetramethyl-1,2,3,4,4a,5,6,7,8,8a-decahydronaphthalene-1-spiro-2'-[6',7'-di-(2,2-diethoxycarbonylvinyl)-4'-hydroxy-2',3'-dihydrobenzofuran]

(10) 6,7-Dihydroxy-2,5,5,8a-tetramethyl-1,2,3,4,4a,5,6,7,8,8a-decahydronaphthalene-1-spiro-2'-[6',7'-di-(2,2-butoxycarbonylvinyl)-4'-hydroxy-2',3'-dihydrobenzofuran]

(11) 6,7-Dihydroxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran)

(12) 6,7-Dihydroxy-2,5,5,8a-tetramethyl-1,2,3,4,4a,5,6,7,8,8a-decahydronaphthalene-1-spiro-2'-(6',7'-dihydroxymethyl-4'-methoxy-2',3'-dihydrobenzofuran)

(13) 6,7-Dihydroxy-2,5,5,8a-tetramethyl-1,2,3,4,4a,5,6,7,8,8a-decahydronaphthalene-1-spiro-2'-(7'-carboxy-6'-formyl-4'-hydroxy-2',3'-dihydrobenzofuran)

(14) 6,7-Dihydroxy-2,5,5,8a-tetramethyl-1,2,3,4,4a,5,6,7,8,8a-decahydronaphthalene-1-spiro-2'-(6'-carboxy-7'-formyl-4'-hydroxy-2',3'-dihydrobenzofuran)

(15) 6,7-Dihydroxy-2,5,5,8a-tetramethyl-1,2,3,4,4a,5,6,7,8,8a-decahydronaphthalene-1-spiro-2'-(7'-carboxy-6'-formyl-4'-methoxy-2',3'-dihydrobenzofuran)

(16) 6,7-Dihydroxy-2,5,5,8a-tetramethyl-1,2,3,4,4a,5,6,7,8,8a-decahydronaphthalene-1-spiro-2'-[6',7'-di-(2,2-dicyanovinyl)-4'-ethoxy-2',3'-dihydrobenzofuran]

(17) 6,7-Dihydroxy-2,5,5,8a-tetramethyl-1,2,3,4,4a,5,6,7,8,8a-decahydronaphthalene-1-spiro-2'-[6',7'-di-(2-cyano-2-carboxyvinyl)-4'-propoxy-2',3'-dihydrobenzofuran]

(18) 6,7-Dihydroxy-2,5,5,8a-tetramethyl-1,2,3,4,4a,5,6,7,8,8a-decahydronaphthalene-1-spiro-2'-[7'-carboxy-6'-(2,2-dicyanovinyl)-4'-hydroxy-2',3'-dihydrobenzofuran]

(19) 6,7-Dihydroxy-2,5,5,8a-tetramethyl-1,2,3,4,4a,5,6,7,8,8a-decahydronaphthalene-1-spiro-2'-[7'-carboxy-6'-(2-cyano-2-carboxyvinyl)-4'-ethoxy-2',3'-dihydrobenzofuran]

(20) 6,7-Dipropionyloxy-2,5,5,8a-tetramethyl-1,2,3,4,4a,5,6,7,8,8a-decahydronaphthalene-1-spiro-2'-(6',7'diformyl-4'-propionyloxy-2',3'-dihydrobenzofuran)

(21) 6,7-Diacetyloxy-2,5,5,8a-tetramethyl-1,2,3,4,4a,5,6,7,8,8a-decahydronaphthalene-1-spiro-2'-[6',7'-(2,2-dicyanovinyl)-4'-acetyloxy-2',3'-dihydrobenzofuran]

(22) 6,7-Dibutyryloxy-2,5,5,8a-tetramethyl-1,2,3,4,4a,5,6,7,8,8a-1-spiro-2'-[6',7'-di-(2-cyano-2-ethoxycarbonylvinyl)-4'-butyryloxy-2',3'-dihydrobenzofuran]

(23) 6,7-Diacetyloxy-2,5,5,8a-tetramethyl-1,2,3,4,4a,5,6,7,8,8a-decahydronaphthalene-1-spiro-

(24) 6,7-Diacetyloxy-2,5,5,8a-tetramethyl-1,2,3,4,4a,5,6,7,8,8a-decahydronaphthalene-1-spiro-2'-[6',7'-di-(2,2-diethoxycarbonylvinyl)-4'-acetyloxy-2',3'-dihydrobenzofuran]

(25) 6,7-Diacetyloxy-2,5,5,8a-tetramethyl-1,2,3,4,4a,5,6,7,8,8a-decahydronaphthalene-1-spiro-2'-(6',7'-diacetyloxymethyl-4'-acetyloxy-2',3'-dihydrobenzofuran)

(26) 7-Acetyloxy-6-hydroxy-2,5,5,8a-tetramethyl-1,2,3,4,4a,5,6,7,8,8a-decahydronaphthalene-1-spiro-2'-(6',7'-diacetyloxymethyl-4'-acetyloxy-2',3'-dihydrobenzofuran)

(27) 6,7-Diacetyloxy-2,5,5,8a-tetramethyl-1,2,3,4,4a,5,6,7,8,8a-decahydronaphthalene-1-spiro-2'-(7'-carboxy-6'-formyl-4'-acetyloxy-2',3'-dihydrobenzofuran)

(28) 6,7-Dipropionyloxy-2,5,5,8a-tetramethyl-1,2,3,4,4a,5,6,7,8,8a-decahydronaphthalene-1-spiro-2'-(7'-carboxy-6'-formyl-4'-methoxy-2',3'-dihydrobenzofuran)

(29) 6,7-Diacetyloxy-2,5,5,8a-tetramethyl-1,2,3,4,4a,5,6,7,8,8a-decahydronaphthalene-1-spiro-2'-[6',7'-di-(2,2-dicyanovinyl)-4'-ethoxy-2',3'-dihydrobenzofuran]

(30) 6,7-Diisobutyryloxy-2,5,5,8a-tetramethyl-1,2,3,4,4a,5,6,7,8,8a-decahydronaphthalene-1-spiro-2'-[6',7'-di-(2-cyano-2-carboxyvinyl)-4'-propoxy-2',3'-dihydrobenzofuran]

(31) 6,7-Diacetyloxy-2,5,5,8a-tetramethyl-1,2,3,4,4a,5,6,7,8,8a-decahydronaphthalene-1-spiro-2'-[7'-carboxy-6'-(2,2-dicyanovinyl)-4'-acetyloxy-2',3'-dihydrobenzofuran]

(32) 6,7-Isopropylidenedioxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran)

(33) 6,7-Isopropylidenedioxy-2,5,5,8a-tetramethyl-1,2,3,4,4a,5,6,7,8,8a-decahydronaphthalene-1-spiro-2'-[6',7'-di-(2,2-dicyanovinyl)-4'-hydroxy-2',3'-dihydrobenzofuran]

(34) 6,7-Ethylidenedioxy-2,5,5,8a-tetramethyl-1,2,3,4,4a,5,6,7,8,8a-decahydronaphthalene-1-spiro-2'-[6',7'-di-(2-cyano-2-ethoxycarbonylvinyl)-4'-hydroxy-2',3'-dihydrobenzofuran]

(35) 6,7-Isopropylidenedioxy-2,5,5,8a-tetramethyl-1,2,3,4,4a,5,6,7,8,8a-decahydronaphthalene-1-spiro-2'-[6',7'-di-(2-cyano-2-isopropoxycarbonylvinyl)-4'-acetyloxy-2',3'-dihydrobenzofuran]

(36) 6,7-Methylenedioxy-2,5,5,8a-tetramethyl-1,2,3,4,4a,5,6,7,8,8a-decahydronaphthalene-1-spiro-2'-[6',7'-di-(2-cyano-2-carboxyvinyl)-4'-hydroxy-2',3'-dihydrobenzofuran]

(37) 6,7-Isopropylidenedioxy-2,5,5,8a-tetramethyl-1,2,3,4,4a,5,6,7,8,8a-decahydronaphthalene-1-spiro-2'-[6',7'-di-(2,2-dicyanovinyl)-4'-acetyloxy-2',3'-dihydrobenzofuran]

(38) 6,7-Propylidenedioxy-2,5,5,8a-tetramethyl-1,2,3,4,4a,5,6,7,8,8a-decahydronaphthalene-1-spiro-2'-[6',7'-di-(2-carboxyvinyl)-4'-hydroxy-2',3'-dihydrobenzofuran]

(39) 6,7-Isopropylidenedioxy-2,5,5,8a-tetramethyl-1,2,3,4,4a,5,6,7,8,8a-decahydronaphthalene-1-spiro-2'-[6',7'-di-(2,2-diethoxycarbonylvinyl)-4'-hydroxy-2',3'-dihydrobenzofuran]

(40) 6,7-Isopropylidenedioxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran)

(41) 6,7-Isopropylidenedioxy-2,5,5,8a-tetramethyl-1,2,3,4,4a,5,6,7,8,8a-decahydronaphthalene-1-spiro-2'-(6',7'-diacetyloxymethyl-4'-acetyloxy-2',3'-dihydrobenzofuran)

(42) 6,7-Isopropylidenedioxy-2,5,5,8a-tetramethyl-1,2,3,4,4a,5,6,7,8,8a-decahydronaphthalene-1-spiro-2'-(6',7'-dihydroxymethyl-4'-methoxy-2',3'-dihydrobenzofuran)

(43) 6,7-Isopropylidenedioxy-2,5,5,8a-tetramethyl-1,2,3,4,4a,5,6,7,8,8a-1-spiro-2'-(7'-carboxy-6'-formyl-4'-hydroxy-2',3'-dihydrobenzofuran)

(44) 6,7-Propylidenedioxy-2,5,5,8a-tetramethyl-1,2,3,4,4a,5,6,7,8,8a-decahydronaphthalene-1-spiro-2'-(7'-carboxy-6'-formyl-4'-acetyloxy-2',3'-dihydrobenzofuran)

(45) 6,7-Butylidenedioxy-2,5,5,8a-tetramethyl-1,2,3,4,4a,5,6,7,8,8a-decahydronaphthalene-1-spiro-2'-(7'-carboxy-6'-formyl-4'-methoxy-2',3'-dihydrobenzofuran)

(46) 6,7-Isopropylidenedioxy-2,5,5,8a-tetramethyl-1,2,3,4,4a,5,6,7,8,8a-decahydronaphthalene-1-spiro-2'-[6',7'-di-(2,2-dicyanovinyl)-4'-ethoxy-2',3'-dihydrobenzofuran]

(47) 6,7-Isopropylidenedioxy-2,5,5,8a-tetramethyl-1,2,3,4,4a,5,6,7,8,8a-decahydronaphthalene-1-spiro-2'-[6',7'-di-(2-cyano-2-carboxyvinyl)-4'-acetyloxy-2',3'-dihydrobenzofuran]

(48) 6,7-Isopropylidenedioxy-2,5,5,8a-tetramethyl-1,2,3,4,4a,5,6,7,8,8a-decahydronaphthalene-1-spiro-2'-[7'-carboxy-6'-(2-cyano-2-carboxyvinyl)-4'-hydroxy-2',3'-dihydrobenzofuran]

(49) 7-Acetyloxy-6-oxo-2,5,5,8a-tetramethyl-1,2,3,4,4a,5,6,7,8,8a-decahydronaphthalene-1-spiro-2'-(6',7'-diacetyloxymethyl-4'-acetyloxy-2',3'-dihydrobenzofuran)

(50) 7-Acetyloxy-6-oxo-2,5,5,8a-tetramethyl-1,2,3,4,4a,5,6,7,8,8a-decahydronaphthalene-1-spiro-2'-[6',7'-di-(2,2-dicyanovinyl)-4'-acetyloxy-2',3'-dihydrobenzofuran]

(51) 7-Acetyloxy-6-oxo-2,5,5,8a-tetramethyl-1,2,3,4,4a,5,6,7,8,8a-decahydronaphthalene-1-spiro-2'-[6',7'-di-(2-cyano-2-ethoxycarbonylvinyl)-4'-acetyloxy-2',3'-dihydrobenzofuran]

(52) 7-Acetyloxy-6-oxo-2,5,5,8a-tetramethyl-1,2,3,4,4a,5,6,7,8,8a-decahydronaphthalene-1-spiro-2'-[6',7'-di-(2-cyano-2-isopropoxycarbonylvinyl)-4'-methoxy-2',3'-dihydrobenzofuran]

(53) 7-Propionyloxy-6-oxo-2,5,5,8a-tetramethyl-1,2,3,4,4a,5,6,7,8,8a-decahydronaphthalene-1-spiro-2'-[6',7'-di-(2,2-butoxycarbonylvinyl)-4'-propionyloxy-2',3'-dihydrobenzofuran]

(54) 7-Acetyloxy-6-oxo-2,5,5,8a-tetramethyl-1,2,3,4,4a,5,6,7,8,8a-decahydronaphthalene-1-spiro-2'-[6',7'-di-(2-cyano-2-carboxyvinyl)-4'-propoxy-2',3'-dihydrobenzofuran]

(55) 4-Hydroxy-8-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene)

(56) 4,6-Dihydroxy-8-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene)

(57) 6-Hydroxy-4-isopropoxy-8-oxo-2,3,6,8-tetrahydrofuro[3,4-g]benzofuran-2-spiro-1'-(6',7'-dihydroxy-2′,5′,5′,8′a-tetramethyl-1′,2′,3′,4′,4′a,5′,6′,7′,8′,- 8′a-decahydronaphthalene)
(58) 4-Propionyloxy-8-oxo-2,3,6,8-tetrahydro-furo[3,4-g]benzofuran-2-spiro-1′-(6′,7′-dipropionyloxy-2′,5′,5′,8′a-tetramethyl-1′,2′,3′,4′,4′a,5′,6′,7′,8′,8′a-decahydronaphthalene)
(59) 4-Acetyloxy-6-hydroxy-8-oxo-2,3,6,8-tetrahydrofuro[3,4-g]benzofuran-2-spiro-1′-(6′,7′-diacetyloxy-2′,5′,5′,8′a-tetramethyl-1′,2′,3′,4′,4′a,5′,6′,7′,8′,8′a-decahydronaphthalene)
(60) 4-Butyryloxy-6-hydroxy-8-oxo-2,3,6,8-tetrahydrofuro[3,4-g]benzofuran-2-spiro-1′-(7′-butyryloxy-6′-hydroxy-2′,5′,5′,8′a-tetramethyl-1′,2′,3′,4′,4′a,5′,6′,7′,8′,8′a-decahydronaphthalene)
(61) 6-Hydroxy-4-propoxy-8-oxo-2,3,6,8-tetrahydrofuro[3,4-g]benzofuran-2-spiro-1′-(6′,7′-propionyloxy-2′,5′,5′,8′a-tetramethyl-1′,2′,3′,4′,4′a,5′,6′,7′,8′,8′a-decahydronaphthalene)
(62) 4-Hydroxy-8-oxo-2,3,6,8-tetrahydro-furo[3,-4-g]benzofuran-2-spiro-1′-(6′,7′-isopropylidenedioxy-2′,5′,5′,8′a-tetramethyl-1′,2′,3′,4′,4′a,5′,6′,7′,8′,8′a-decahydronaphthalene)
(63) 4,6-Dihydroxy-8-oxo-2,3,6,8-tetrahydro-furo[3,-4-g]benzofuran-2-spiro-1′-(6′,7′-isopropylidenedioxy-2′,5′,5′,8′a-tetramethyl-1′,2′,3′,4′,4′a,5′,6′,7′,8′,8′a-decahydronaphthalene)
(64) 6-Hydroxy-4-isopropoxy-8-oxo-2,3,6,8-tetrahydrofuro[3,4-g]benzofuran-2-spiro-1′-(6′,7′-propylidenedioxy-2′,5′,5′,8′a-tetramethyl-1′,2′,3′,4′,4′a,5′,6′,7′,8′,8′a-decahydronaphthalene)
(65) 6-Hydroxy-4-acetyloxy-8-oxo-2,3,6,8-tetrahydro furo[3,4-g]benzofuran-2-spiro-1′-(6′,7′-isopropylidenedioxy-2′,5′,5′,8′a-tetramethyl-1′,2′,3′,4′,4′a,5′,6′,7′,8′,8′a-decahydronaphthalene)
(66) 4-Hydroxy-8-oxo-2,3,6,8-tetrahydro-furo[3,4-g]--benzofuran-2-spiro-1′-(7′-acetyloxy-6-oxo-2′,5′,5′,8′a-tetramethyl-1′,2′,3′,4′,4′a,5′,6′,7′,8′,8′a-decahydronaphthalene)
(67) Disodium 6,7-dihydroxy-2,5,5,8a-tetramethyl-1,2,3,4,4a,5,6,7,8,8a-decahydronaphthalene-1-spiro-2′-(7′carboxylate-6′-formyl-4′-oxide-2′,3′-dihydrobenzofuran)

The nomenclature of the above compounds is based on the position numbers shown in the general formula (I) above. Those compounds of the general formula (I) in which $R^2$ and $R^3$ form a lactone ring together with the two carbon atoms to which they are attached are named in accordance with the position numbers shown in the following skeletal formula (I′).

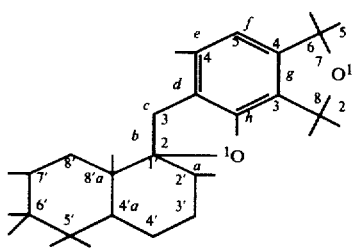

(I′)

II. PROCESSES

Processes for preparing the sesquiterpene derivatives of this invention of the general formula (I) are described in detail below.

1(a). Preparation of Compounds of the General Formula (Ia)

The sesquiterpene derivatives of the general formula (I) of the invention can be prepared by various methods depending on the types of substituents present therein. For example, a compound of the general formula (I) in which both $R^1$ and $R^5$ are hydrogen atoms, $R^2$ and $R^3$ are both formyl groups and $R^4$ and $R^6$ are both hydroxyl groups, shown below by the general formula (Ia)

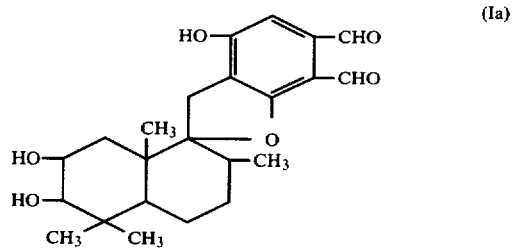

(Ia)

can be prepared by utilizing the following known microorganisms belonging to the genus Stachybotrys, or microorganisms of the genus Stachybotrys newly isolated as a result of this invention.
*Stachybotrys alternans* IFO 9355,
*Stachybotrys chartarum* IFO 5369,
*Stachybotrys chartarum* IFO 7222,
*Stachybotrys cylindrospora* IFO 8858,
Stachybotrys echinata IFO 7525, and
*Stachybotrys reniformis* IFO 7067.

The microorganisms newly isolated are new strains belonging to the genus Stachybotrys as is described below, and they have been named *Stachybotrys complementi* nov sp. K-76 (hereinafter referred to as Stachybotrys sp. K-76), *Stachybotrys complementi* nov sp. T-789 (hereinafter referred to as Stachybotrys sp. T-789) and *Stachybotrys (Memmoniella) echinata* var. T-791 (hereinafter referred to as Stachybotrys sp. T-791).

(A) Place of Occurrence (1) Stachybotrys sp. K-76

This strain was isolated from the soil at Ishigaki City, Okinawa, Japan.

(2) Stachybotrys sp. T-789

This strain was isolated from the soil at Naruto City, Tokushima, Japan.

(3) Stachybotrys sp. T-791

This strain was isolated from the soil as Tokushima City, Tokushima, Japan.

(B) Characteristics on Various Culture Media (1) Stachybotrys sp. K-76

The culture characteristics of this strain on various culture media based on visual and microscopic observations (FIGS. 1 and 2) are as follows:

(a) Visual Observation

Very good growth is observed on various culture media usually employed in cultivating mold fungi, but the adhesion of phialospores is not necessarily good except on oatmeal-agar medium. The growth conditions on typical media are shown below.

(i) Malt Extract-Agar Medium

The growth is relatively slow, and by cultivation at 27° C. for 30 days, a large colony with a size of 30 to 35 mm forms. The colony grows in a circular shape, and the colony periphery has a large erose form. The surface of the colony is smooth, and aerial hyphae stretch thickly like a circular mat at the colony center and grow densely. The colony gradually turns from white at the early stage of cultivation to light ivory (Li Ivory, 2ca). Two weeks after the beginning of cultivation, phialospores begin to form slightly, but are scarcely perceptible to the naked eye. Sclerotium and other sexual sporogenous organs are not formed. The color of the back surface of the colony ranges from colorless to copper tan (Copper Tan, 5ie). A copper tan (Copper Tan, 5ie) soluble pigment is produced.

(ii) Potato Glucose Agar Medium

The growth is good, and by cultivation at 27° C. for 30 days, the colony size reached 45 to 47 mm. The colony growth is convex at the colony center, and the colony periphery has an erose form. The colony presents concentric circles or folds starting at the colony center. From the initial stage of cultivation, the colony is thickly covered with white to pearl pink (Pearl Pink, 4ca) hyphae. As cultivation progresses, the color of the colony becomes black gray (Gray, i). A great deal of phialospores masses are formed. Large amounts of liquid droplets are observed. The color of the back surface ranges from rust tan (Rust Tan, 5ie) to light rose brown (Li Rose Brown, 6½lg). A soluble pigment produced has a butter scotch (Butter Scotch, 3ne) color, but the color is faint.

(iii) Czapek Agar Medium

The growth is good, and by cultivation at 27° C. for 30 days, the colony size reaches 40 to 45 mm. The colony presents a concentric fold, and the colony has an umbonate at the colony center. The periphery of the colony is undulate. The color of the back surface of the colony is luggage tan (Luggage Tan, 4ne). At the colony surface, colorless to white hyphae adhere thinly in a concentric form from the central part which is not covered with aerial hyphae having a toast tan color (Toast Tan, 4lg). No liquid droplets are observed, but the central part of the colony is hygroscopic. Phialospores are scarcely formed. The soluble pigment is faint, and has a gold color (Gold, 2le).

(iv) Oatmeal Agar Medium

The growth is very rapid, and by cultivation at 27° C. for 30 days, the colony size reaches 60 to 70 mm. The colony is thin and flat, and from the initial stage of cultivation, colorless to white hyphae are formed on the entire surface of the colony. Erect hyphae, 3 to 4 mm in size, form only at the central portion of the colony, but are not dense. Two weeks after the beginning of cultivation, the adhesion of phialospore spreads over the entire surface of the colony, and the color of the colony turns light olive drab (Li Olive Drab, 1li). The color of the back surface of the colony is beige brown (Beige Brown, 3ig) to tan (Tan, 3ie). The soluble pigment produced is faint colonial yellow (Colonial Yellow, 2ca).

(2) Stachybotrys sp. T-789

Figure 3:
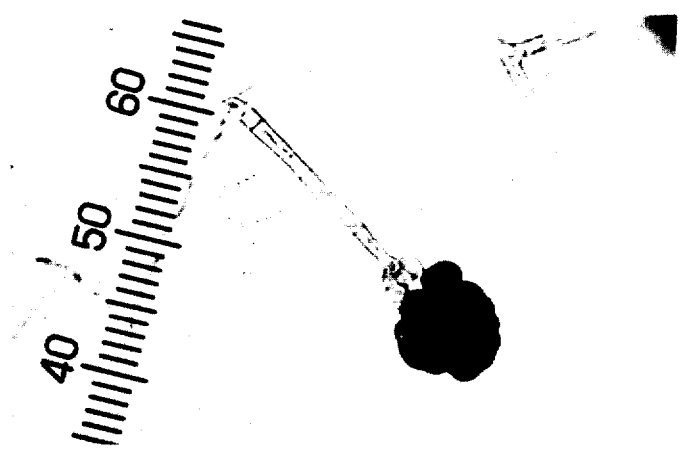
FIG. 3 is a microphotograph of *Stachybotrys complementi* nov sp. T-789.

The culture characteristics of T-789 strain, which is Fungi-Imperfecti, on various culture media were observed visually and microscopically (as shown in FIG. 3), and the results are described above. The morphological characteristics of the T-789 strain by microscopic observation agree well with those of Stachybotrys sp. K-76. However, there are differences in properties on culture media. On the following two media, the characteristics differ most markedly.

(a) Visual Observation

(i) Malt Extract Agar Medium

The growth is very slow, and by cultivation at 27° C. for 30 days, the colony size reaches 17 to 20 mm. The peripheral part of the colony grows in an undulating manner and is restricted at the center. The colony shows an umbonate form of the colony, and a radial fold on the periphery of the colony. Aerial hyphae adhere thinly to the entire surface of the colony. At the initial culture stage, the hyphae are white, and conidia are formed gradually. The central part of the colony assumes a mole color (Mole, l), and the conidia grow densely. Conidia formation is ring-like toward the periphery of the colony. The color of the back surface of the colony is cork tank (Cork Tan, 4ie). The soluble pigment is abundant, and amber in color (Amber, 3le).

(ii) Czapek Agar Medium

The growth is good, and by cultivation at 27° C. for 30 days, the growth reaches 45 mm. The center of the colony is convex and the colony forms a radial fold. The peripheral part of the colony shows an undulate growth. White aerial hyphae adhere thinly in a concentric circular form outwardly from the central convex part of the colony. Conidia form concentrically only at the peripheral part of the colony. The hyphae are in the dissolved state at the convex portion, and are very hygroscopic. The color of the back surface of the colony is mustard brown (Mustard Brown, 2pi). No soluble pigment is produced.

(3) Stachybotrys sp. T-791

The culture characteristics of T-791, which is Fungi Imperfecti, on various culture media based on visual and microscopic observations (shown in FIG. 4) are as follows:

(a) Visual Observation

(i) Malt Extract Agar Medium

The growth is rapid and irregular. The color of the back surface of the colony is tan (Tan, 3ie) to dark brown (Dk Brown, 2pn). The colony is flat, and conidia formation is good. The color of the hyphae is biscuit (Biscuit, 2ec) to tan (Tan, 3ie) and liquid droplets which are exuded are observed. No soluble pigment is produced.

(ii) Potato Glucose Medium

The growth is very rapid, and by cultivation at 27° C. for 30 days, the colony size reaches 70 mm. The peripheral part of the colony spreads dendritically, and adhered white hyphae are observed. A large number of liquid droplets are present. Hardly any spore formation is observed. The color of the back surface of the colony is light amber (Li Amber, 3ie). No soluble pigment is formed.

(iii) Czapek's Dox Agar Medium

The growth is poor.

(iv) Synthetic Mucor Agar Medium

The growth is poor.

(v) Oatmeal Agar Medium

The growth is very good, so that in two weeks, the Petri dish is covered. The colony is thin and flat. Formation of hyphae is abundant from the initial stage of cultivation, and conidia formation is also rapid. The color of the colony changes from white to dark brown (Dk Brown, 3pn) as cultivation proceeds. Large quantities of liquid droplets occur on the hyphae. No soluble pigment is produced.

(C) Physiological Properties

Stachybotrys K-76, T-789 and T-791 are all aerobic strains, and have the following physiological properties.

|  |  | pH | Temperature |
|---|---|---|---|
| (1) | Stachybotrys sp. K-76 |  |  |
|  | Growth Conditions: | 3.5–11.5 | 15°–35° C. |
|  | Optimal Growth Conditions: | 6.0–9.5 | 20°–32° C. |
| (2) | Stachybotrys sp. T-789 |  |  |
|  | Growth Conditions: | 3.5–11.5 | 15°–38° C. |
|  | Optimal Growth Conditions: | 4.5–10.5 | 20°–32° C. |
| (3) | Stachybotrys sp. T-791 |  |  |
|  | Growth Conditions: | 3.5–11.5 | 15°–38° C. |
|  | Optimal Growth Conditions: | 4.5–9.5 | 20°–30° C. |

(D) Morphological Properties

(1) Stachybotrys sp. K-76

Figure 1:
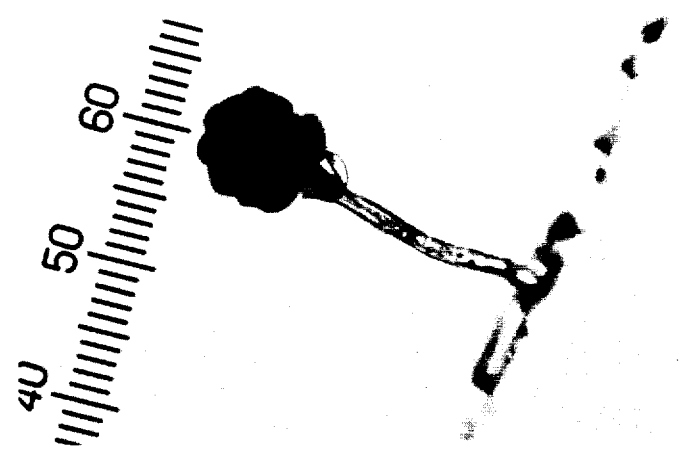

The following are clearly seen from FIGS. 1 and 2. Sclerotium and other sexual reproductive organs are not observed on various culture media, but asexual spores of the phialospore type are seen to form.

Hyphae are formed on various culture media, branch complicatedly, and stretch longitudinally and transversely with a hypha width of 2 to 4$\mu$.

Phialophores simply branch from the hyphae (no branching from one phialophore to another), and have 3 to 4 septa from the foot cells at the base part, they stretch erect or gently curved. The hypha width of the phialophore is 4.3 to 4.7$\mu$ at the base part and 3.6 to 4.5$\mu$ at the central part. The tips of the phialophore are slightly bulged, and from the extreme ends of the phialophore, 3 to 7 ellipsoidal to obclavate erect phialide with a size of 7.9–9.3×3.6–4.7$\mu$ are formed. The phialide are smooth and have a color ranging from colorless to pale yellowish brown. The phialospores are formed connected basipetally from the ends of the phialide. The phialospores do not form straight chains, but become slimy drooping small semi-circular masses, the number of which is 7 to 26. The phialophore are subglobose to oval with a size of 4.9–8.0×3.3–4.7$\mu$, and the surfaces of the phialophore are rough to warty, and the colors of the phialophore are dark ivy (Dk ivy 24po) to grayish black. No membrane due to mucous matter is seen on the phialospore masses.

The taxonomical status of the present strain having the above microbiological properties has been searched through G. L. Barron, *The Genera of Hyphomycetes from Soil*, The Williams & Wilkins Company, Baltimore (1968), J. C. Gilman, *A Manual of Soil Fungi*, The Iowa State University Press, Ames, Iowa (1971), and J. A. von Arx, *The Genera of Fungi Sporelating in Pure Culture*, Verag von J. Cremer 3301 Lehre (1970). According to the taxonomical system of Saccardo, the present strain belongs to Class Hyphomycetes, Family Dematiaceae, Genus Stachybotrys. In other words, the properties of the present strain characterized by the absence of ascocarps and other sexual reproductive organs, the formation of dark brown phialospores from phialide and the gathering of the resulting phialospores in a semicircular form at the top ends of the phialide agree well with the properties of the genus Stachybotrys.

The various characteristics of the present strain have been identified with reference to the above-described search manuals, and literature references such as G. R. Bisby *Trans. Brit. Mycol. Soc.*, 26, 133–143 (1943), R. K. Zuck, *Mycologia*, 38, 69–76 (1946), G. L. Barron, *Can. J. Bot.*, 39, 153–157 (1961), and in comparison with the type strains preserved at the Institute for Fermentation, Osaka, Japan (IFO). As a result, the present strain K-76 has been judged to be most similar to *Stachybotrys lobulata* IFO 5369, because the phialospores of the present K-76 have a rough to warty protrusion and are oval to ellipsoidal. However, differences exist in that *Stachybotrys lobulata* has a phialophore which may reach 1 mm in size, and while the K-76 strain shows simple branching, the *Stachybotrys lobulata* strain has the property that another phialophore branches and stretches from one phialophore. In regard to growth on various culture media, the K-76 strain produces a large quantity of soluble pigment, and conidia formation is very poor on agar media except on potato glucose agar medium and oatmeal agar medium. On the other hand, *Stachybotyrs lobulata* grows very rapidly on various culture media, and a fold-free flat colony is formed. Conidia formation is good on almost all media except on Czapek's Dox agar medium so as to typify the color of the colony. No soluble pigment is produced, or is produced only faintly.

From the above differences, the present strain K-76 has been judged to be a new strain different from *Stachybotrys lobulata*, and the present strain has been named Stachybotrys sp. K-76.

(2) Stachybotrys sp. T-789

From FIG. 3, the following can be seen. This strain has quite the same morphology as Stachybotrys sp. K-76, although there is some difference in colony size.

In the same way as in the Stachybotrys sp. K-76, the above microbiological properties have been compared with the searching manuals and literature references mentioned above and with IFO type strains. Consequently, this strain has been found to be most similar to *Stachybotrys lobulata* IFO 5369 and Stachybotrys sp. K-76. The present strain shows good formation of phialospores on Czapek agar medium. However, the formation of phialospores on Czapek's Dox agar medium is scarcely observed for the first two strains. This is a culture difference.

Furthermore, as stated with regard to Stachybotrys sp. K-76 above, the morphological properties of the present strain are evidently different from *Stachybotrys lobulata*. Furthermore, the optimal growth pH range of the present strain is a pH of 4.5 to 10.5. From this point also, the present strain differs from the K-76 strain.

For the above reason, therefore, the present strain has been regarded as a new strain, and named Stachybotrys sp. T-789.

(3) Stachybotrys sp. T-791

Figure 4:
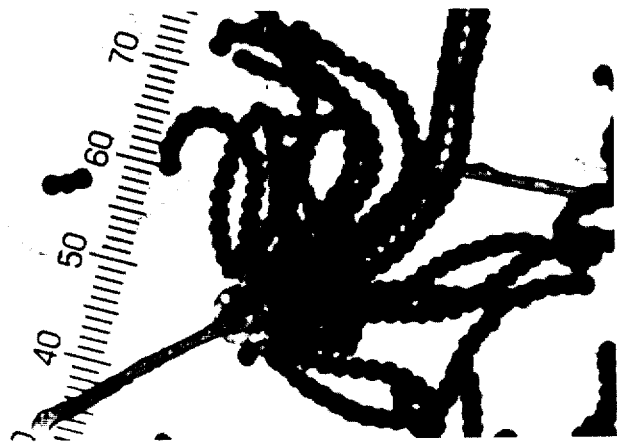
FIG. 4 is a microphotograph of *Stachybotrys echinata* var. T-791.

The following can be seen from FIG. 4. The phialophores simply branch and stand erect. The phialophore tips slightly bulge in a rod form. However, the bulging is not so large as is observed in the type strains of Stachybotrys echinata IFO 7525 and 8856. This strain shows a hypha width of 4.0 to 4.5μ which is slightly larger than the phialophore. The phialophores which branch erect with foot cells from vegetative hyphae or aerial hyphae have two to three septa and have a size of 40–80×3.0–3.5μ. The cellular wall of the phialophore is not echinulate, but smooth.

Three to six phialide form from the bulged portion at the tips of the phialophores. Furthermore, spherical to sub-globose phialospores of one cell having an echinulate protrusion and a size of 4.3–5.2×3.0–4.2μ continuously form basipetally at the tips of the phialide and a chain of 24 to 70 conidia is formed. The phialide has an obclavate form, and has a size of 6.9–10.7×3.5–4.7μ. The phialophores and phialide are colorless, and the phialide has a coffee (Coffee, 3pn) to black color.

The taxonomical status of the present strain with the above-described microbiological properties was searched through the searching manuals set forth in the section dealing with the K-76 strain. As a result, the present strain was found to belong to the genus Stachybotrys (genus Memmoniella). Specifically, the present strain does not possess ascocarps and other sexual reproductive organs, and dark brown phialospores form continuously from the phialide. Long chains of spores are formed. The properties of the present strain T-791 agree with those of the genus Stachybotrys (genus Memmoniella).

The various properties of the present strain have been searched through the aforesaid searching manuals and literature references such as R. K. Zuck Mycologia, 38, 69–76 (1964) and G. Smith, *Trans. Brit. Mycol. Soc.*, 45, 387–394 (1962) and compared with the type strains preserved at IFO. As a result, it has been judged that since phialospores are formed continuously and basipetally from phialide, the strain T-791 belongs to *Memmoniella echinata* termed by Hohnel. However, from the reports of R. K. Zuck and G. Smith supra, the present strain T-791 was considered to be a strain analogous to *Stachybotrys echinata*. Hence, it was compared with *Stachybotrys ethinata* IFO 7525 and IFO 8856.

Morphologically, echinulate protrusions specific to the two type strains are not observed on the cell walls of the phialophores in the present strain T-791. Furthermore, in the type strains, the tips of the phialophores bulge to 2 to 3 times the hypha width of the phialophores, however, no marked bulging is observed in the present strain. Furthermore, the two type strains show good growth on various culture media, especially on potato glucose agar medium, and form circular, somewhat raised colonies, and hyphae adhere abundantly. Furthermore, conspicuous conidia formation is observed. In contrast, the present strain shows a dendritic irregular growth as stated hereinabove, and poor hypha formation and poor conidia formation are observed. From the above microbiological differences, the present strain has been considered to be a new strain, and named Stachybotrys sp. T-791.

The indication of the colors above and hereinafter is in accordance with the method described in *Color Harmony Manual*, Container Corporation of America (1958).

Samples of the new strains, Stachybotrys sp. K-76, Stachybotrys sp. T-789, and Stachybotrys sp. T-791 have been deposited at the Fermentation Research Institute, Agency of Industrial Science and Technology, Japan under deposit numbers FERM-P No. 3801 (ATCC No. 20511), FERM-P No. 3802 (ATCC No. 20512), and FERM-P No. 3803 (ATCC No. 20513), respectively.

1(b). Production of Compound of the General Formula (Ia) by Microorganisms of the Genus Stachybotrys Specifically, the preparation of the compound of the general formula (Ia) by the microorganisms of the genus Stachybotrys described above is achieved in the following manner.

The microorganisms are first cultivated in a medium containing ordinary nutrient sources and additives. Nitrogen sources generally used as a cultivating substrate include, for example, soybean powder, soybean oil, corn steep liquor, yeast extract, dried yeast, oatmeal, meat extract, hydrolyzed casein, ammonium salts, and nitrate salts. Examples of suitable carbon sources are glucose, glycerol, maltose, starch, lactose, sucrose, and molasses. Examples of additives to the culture medium include inorganic salts such as calcium carbonate, sodium chloride, magnesium sulfate, and phosphoric acid. If required, the culture medium may further contain tiny amounts of salts of metals such as iron, copper, manganese, and zinc. Cultivation can be performed in an ordinary aqueous medium containing the above substrate using a surface cultivating technique or a submerged cultivation technique with aeration and stirring. Submerged cultivation with aeration and stirring is preferred. The cultivation can be advantageously carried out at a temperature of about 15° to about 35° C., preferably 20° to 32° C., for a period of usually about 3 to about 7 days under ordinary conditions while maintaining the pH of the culture medium at about 3.5 to about 11.5, preferably 4.5 to 9.5.

After the cultivation, the substance produced is recovered from the culture broth. The method of recovery is not particularly restricted, and various known methods utilizing the physicochemical properties of the substances produced can be employed. Recovery can be accomplished, for example, by a method utilizing the differences in solubility between the products and impurities, a method utilizing the differences in adsorptive power and affinity for ordinary adsorbents such as activated carbon, silica gel, ion exchange resins, or Sephadex (trademark for a product of Pharmacia Fine Chemicals), a method utilizing the differences in the coefficient of distribution between two liquid phases, and a combination of such methods.

More specifically, the culture broth is filtered or centrifuged in a conventional manner to remove the cells. Then, methanol is added to the supernatant liquid, and the mixture is stirred and allowed to stand for 2 to 3 hours. The precipitate is removed by another centrifugal separation. The residue is extracted with the same volume of ethyl acetate, and the solvent is distilled off. The extract is placed into methanol, and the methanol solution is passed through a column of activated carbon, and the solvent is distilled off from the eluate. The residue is gel-filtered using Sephadex Lh-20. The resulting fractions are each subjected to an anti-complement activity test described hereinafter. After fractions are collected, and the solvent is distilled off. Thus, pure 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) of the structural formula (Ia) shown above can be isolated.

2. Preparation of Other Compounds of the General Formula (I)

Sesquiterpene derivatives of the general formula (I) of the present invention other than the compound of the formula (Ia) can be prepared from the compound of the formula (Ia) as a starting material by one of the processes described hereinafter, or by a combination of two or more of these processes. The reactions involved in these processes and the compounds produced are described below.

(A) Process (1)

Compounds of the general formula (I) in which one or both of $R^2$ and $R^3$ represent a carboxyl group (to be referred to hereinafter as compounds (IB)) can be prepared by oxidizing compounds of the formula (I) in which one or both of $R^2$ and $R^3$ represent a formyl group (to be referred to hereinafter as compounds (IA)), for example, compound (Ia).

The oxidation reaction can be performed in accordance with conventional methods of obtaining aromatic carboxylic acids from aromatic aldehyde compounds. Examples of applicable oxidizing methods are a method using an oxidizing agent, a method involving light irradiation in the absence of catalyst, a contact oxidation method in the presence of catalyst using air or oxygen, an electrolytic oxidizing method in the presence of a copper compound or sulfuric acid, and an oxidizing method using an enzyme. In view of the simplicity of operation, etc., the ease of separation and purification of the reaction product, and the yield, etc., a method using an oxidizing agent and a contact oxidation method using air or oxygen are advantageous.

There is no particular restriction on the oxidizing agents which can be used in performing the method using an oxidizing agent. Any conventional inorganic and organic oxidizing agents can be used. Typical examples of inorganic oxidizing agents which can be used include permanganate salts, manganese oxide, manganese pyrophosphate, chromic acid, chromate salts, silver oxide, silver nitrate, Tollens reagent, gold oxide, nickel peroxide, selenium dioxide, chlorine, bromine, iodine, hypochlorous acid, hypobromous acid, perchloric acid, periodic acid, salts of the above-described hypohalous acids and perhalic acids, nitric acid, nitrous acid, nitrogen tetroxide, nitrogen dioxide, cobalt salts such as cobaltic sulfate or cobaltic acetate, cerium salts such as cerium sulfate, cerium oxide and cerium perchlorate, hydrogen peroxide, and ozone. Examples of organic oxidizing agents which can be used are N-bromosuccinimide, N-chlorosuccinimide, sodium N-chloro-p-toluenesulfonamide, sodium-N-chlorobenzenesulfonamide, azo compounds such as ethyl azodicarboxylate and 4-phenyl-1,2,4-triazoline-3,5-dione, and percarboxylic acids such as performic acid, peracetic acid, monoperphthalic acid, trifluoroperacetic acid, perbenzoic acid, and m-chloroperbenzoic acid.

Of these oxidizing agents, permanganate salts, silver oxide, hydrogen peroxide, chromic acid, peracetic acid, and perbenzoic acid are preferred, and permanganate salts and silver oxide are most preferred.

Preferably, the oxidizing method using an oxidizing agent is carried out in a suitable solvent. Examples of suitable solvents which can be used are water and dry or wet organic solvents, e.g., alcohols such as methanol and ethanol, pyridine, ethers such as dioxane, tetrahydrofuran and diethyl ether, ketones such as acetone and methyl ethyl ketone, carboxylic acids such as acetic acid and propionic acid, esters such as ethyl acetate, aromatic hydrocarbons such as benzene or chlorobenzene, hexamethylphosphoramide, dimethylformamide, and dimethyl sulfoxide. A suitable amount of the oxidizing agent is about 1 to about 10 equivalents, preferably 1 to 2 equivalents, per formyl group of the starting compound (IA). The reaction can be carried out at about −10 to about 100° C., preferably 0° to 50° C., for about 30 minutes to about 24 hours.

The contact oxidizing method using an oxygen containing gas such as air or oxygen may be performed, for example, by bubbling oxygen or air into an aqueous solution of sodium hydroxide or potassium hydroxide in the absence of a catalyst, or by bubbling air or oxygen into an aqueous solution in the presence of an inorganic salt catalyst such as cobalt nitrate, manganese acetate, or cobalt acetate, or in the presence of a radical initiator such as benzoyl peroxide, or under irradiation of light. Among these procedures, a contact auto-oxidation method comprising bubbling air or oxygen in the absence of a catalyst into an aqueous alkaline solution is especially advantageous. This reaction can be completed by stirring the reaction system usually at normal temperature (about 1°–30° C.) to about 100° C., preferably 40° to 50° C., for about 30 minutes to about 24 hours, usually for about 30 minutes to 2 hours.

After the above oxidation reaction, the oxidizing agent, if used, is decomposed with a reducing agent, and then inorganic by-products are removed by filtration, neutralization, vacuum distillation, etc. Where air, etc., is bubbled into the reaction system, the reaction mixture is preferably treated with activated carbon, and then acidified, e.g., with hydrochloric acid, to precipitate crystals. The reaction mixture is extracted with organic solvent such as ethyl acetate, and then subjected to a conventional separation purification procedure such as column chromatography or fractional crystallization. Thus, the desired compound (IB) can be separated.

Of the compounds obtained by the above-described procedure, a compound in which one of $R^2$ and $R^3$ is a formyl group and the other of $R^2$ and $R^3$ is a carboxyl group (this compound will be referred to hereinafter specifically as compound (Ib)) has a structure (Ib$_1$)) having a lactole ring in the crystalline state. In a solvent, especially in a basic solvent, compound (Ib) is present as an equilibrium mixture of compound (Ib$_1$) and its tautomer, the monocarboxylic acid compound (Ib$_2$) shown below.

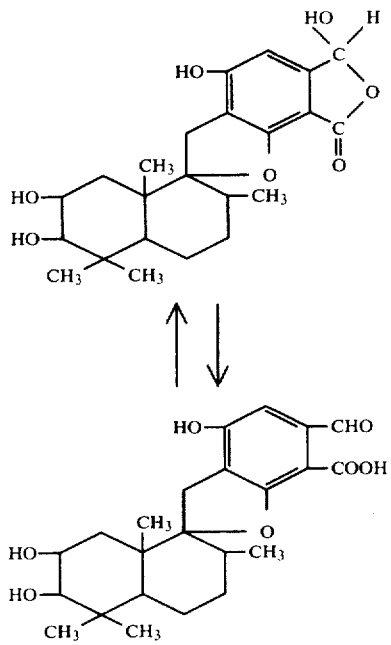

The above structures represent an example of the compound of the formula (I) in which $R^1$ and $R^5$ are hydrogen atoms, $R^2$ is a formyl group, $R^3$ is a carboxyl group, and $R^4$ and $R^6$ are hydroxyl groups.

This structure was confirmed by dissolving the compound (Ib$_1$) (crystalline) in dimethyl sulfoxide, and measuring the NMR spectrum thereof with time. Twenty minutes after dissolution, a peak was observed at 9.89 ppm which is a characteristic signal of an aldehyde proton (—C<u>H</u>O) in addition to a peak at 6.36 ppm which is a characteristic signal of a lactole. The integrated ratio of the former peak to the latter peak was about 73:about 27. Two hours after dissolution, the peak at 9.89 ppm somewhat increased, and the integrated ratio reached about 70:30. This integrated ratio attained two hours after dissolution scarcely changed thereafter. This result demonstrated that the compound (Ib$_1$) and the compound (Ib$_2$) were present as a 7:3 molar equilibrium mixture in the above solvent. When methanol or pyridine was used as the solvent, a similar NMR spectroscopic analysis could not lead to a confirmation of the compound (Ib$_2$) which is a tautomer of the compound (Ib$_1$).

(B) Process (2)

Compounds of the formula (I) in which at least one of $R^2$ and $R^3$ represents a hydroxymethyl group (to be referred to hereinafter as compounds (IC)) can be prepared by (1) reducing the formyl or carboxyl groups of the compounds (IA) or (IB), or (2) reducing compounds of the general formula (I) in which $R^2$ and $R^3$ combine to form a lactone ring of the formula

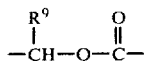

in which $R^9$ is a hydrogen atom or a hydroxyl group (to be referred to hereinafter as compounds (ID)).

The above reduction can be performed using the following two methods.

The reduction of the formyl groups can be performed using various conventional methods for reducing aromatic aldehydes to aromatic alcohols, for example, by using a reducing agent, a catalytic reducing method, or an electrolytic reducing method.

In the method using a reducing agent, examples of suitable reducing agents which can be used are aluminum hydride compounds such as lithium aluminum hydride, sodium aluminum hydride, sodium triethoxyaluminum hydride, and sodium bis(2-methoxyethoxy)aluminum hydride, boron hydride compounds such as sodium borohydride, lithium borohydride, sodium borohydride cyanide and diborane, organic tin hydrides such as tri-n-butyl tin hydride, diphenyl tin hydride and triethyl tin hydride, and hydrosilanes such as dimethylphenylsilane and triethylsilane.

Various conventional catalysts can be used in the catalytic reducing method. Examples of suitable catalyst which can be used are palladium black, palladium on carbon, Raney nickel, and platinum oxide. A suitable amount of catalyst ranges from about 1 to about 50% by weight, preferably 5 to 15% by weight, based on the weight of the starting compound represented by the general formula (IA), (IB) or (ID).

The electrolytic reducing method can be carried out, for example, by using mercury, lead, platinum, zinc, nickel, palladium, graphite, etc., as a cathode, and passing a direct current of a voltage of about 2 to about 12 V, preferably 4 to 6 V, through a neutral or alkaline solution containing the compound.

Of the above reducing methods, a method using a reducing agent is advantageous in view of the ease of handling, and the reasonable cost of treatment. The use of sodium borohydride as a reducing agent is most advantageous. In more detail, this method is carried out in an inert solvent, for example, an aqueous solution of an alkali such as sodium hydroxide or potassium hydroxide, water, a lower alcohol such as methanol or ethanol, an ether such as tetrahydrofuran or dioxane, or a mixture of these solvents. A suitable amount of the reducing agent used is usually at least about 1 equivalent, preferably 1 to 8 equivalents, based on the formyl groups of the starting compound to be reduced. The reaction temperature is usually about 0° to about 60° C., preferably 5° to 25° C. Generally, the reaction is completed in about 30 minutes to about 10 hours.

When the compound (Ib) is used as a starting material in the reducing reaction, a basic material must be introduced into the reaction system in advance to open the lactole ring. This is because, under neutral or acidic conditions, the compound (Ib) is present as a lactole compound of which the compound of the structure (Ib$_1$) given hereinabove is typical, which is very stable and which cannot be readily reduced. For this purpose, the reducing agents, solvents and reaction conditions as described above should be employed in the presence of a basic material such as sodium hydroxide, potassium hydroxide, sodium carbonate, potassium carbonate or sodium hydrogen carbonate. A suitable amount of the basic material is about 1 mol or more per mol of the starting material represented by the general formula (Ib). Preferably, in the presence of the basic material, the above-described starting compound is heated with stirring at about 0° to about 80° C., preferably 40° to 60° C., for about 1 to about 8 hours together with at least about 4 equivalents, preferably 4 to 16 equivalents, of sodium borohydride as a reducing agent in a conventional inert solvent such as water, methanol, ethanol, tetrahydrofuran and dioxane, either individually or as a mixture of solvents.

Reduction of the carboxyl groups in the compound (IB) or of a compound (IC) obtained by the above-described procedure in which one of $R^2$ and $R^3$ is a hydroxymethyl group and the other is a carboxyl group and they combine to form a lactone ring (to be referred to hereinafter as compound (Id)) can be performed in the following manner. Compound (Id) is reacted with at least about 1 equivalent, preferably 1 to 8 equivalents, of lithium aluminum hydride as a reducing agent per equivalent of compound (Id) in a conventional inert solvent such as dioxane or diethyl ether at about 0° to about 60° C., preferably 5° to 25° C., for about 30 minutes to about 10 hours.

(C) Process (3)

Compounds of the formula (I) in which $R^2$ and $R^3$ combine to form a lactone ring of the formula

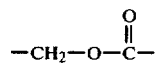

(to be referred to as compounds (Id)) can be easily prepared by cyclizing with release of water compounds of the formula (IC) obtained by the method described above in which one of $R^2$ and $R^3$ represents a hydroxymethyl group and the other of $R^2$ and $R^3$ represents a carboxyl group, in the absence of a solvent or in the presence of a suitable solvent.

The above cyclizing with release of water reaction can be performed by directly heating compounds of the formula (IC), as the starting material, to about 100 to about 200° C. Alternatively, the starting material is dissolved in a suitable inert solvent, and heated in the presence of a catalytic amount (about 0.01 to about 50% by weight, preferably 0.01% to 10% by weight, based on the weight of the starting material) of an acidic compound at about 0° to about 200° C., preferably 60° to 150° C., for about 10 minutes to about 24 hours, generally 2 to 10 hours. Examples of suitable solvents which can be used are aromatic hydrocarbons such as benzene and toluene, halogenated hydrocarbons such as dichloromethane, dichloroethane and chloroform, ethers such as dimethyl ether, tetrahydrofuran, and dioxane, glycols such as ethylene glycol, and lower alcohols such as ethanol and methanol. Examples of suitable acidic compounds which can be used include, for example, hydrogen chloride, hydrochloric acid, phosphoric acid, polyphosphoric acid, boron trifluoride, perchloric acid, trichloromethanesulfonic acid, trifluoroacetic acid, naphthalenesulfonic acid, p-toluenesulfonic acid, benzenesulfonic acid, thionyl chloride and acetone dimethyl acetal.

(D) Process (4)

Compounds of the general formula (I) in which one or both of $R^2$ and $R^3$ represent a group of the formula —CH=CR$^7$R$^8$ in which $R^7$ and $R^8$ are as defined above (to be referred to hereinafter as compounds (IE)) can be prepared by dehydrocondensing compounds (IA) with active methylene compounds of the general formula (II):

wherein $R^7$ and $R^8$ are as defined above, in the presence of a catalyst.

The dehydrocondensation reaction can be performed in the absence of solvent. However, the dehydrocondensation reaction can be advantageously carried out in a conventional inert solvent, for example, an aqueous solution of an alkali such as sodium hydroxide, water, an alcohol such as methanol or ethanol, an ether such as dioxane or tetrahydrofuran, an aromatic hydrocarbon such as benzene or toluene, a tertiary amine such as pyridine or triethylamine, or a halogenated hydrocarbon such as methylene chloride, chloroform or carbon tetrachloride. If an aqueous alkali solution, pyridine, and triethylamine are used as a solvent, they also act as a catalyst, hence, it is not necessary to add another catalyst. When other solvents are used, a catalyst, for example, an amino acid such as β-alanine, a cyclic amine such as piperidine or morpholine, ammonia, an amine such as ethylamine, diethylamine or butylamine, acetate salts of these amines, an alkali metal acetate such as sodium acetate or potassium acetate, or an alkali metal alcoholate such as sodium ethylate or sodium methylate, must be used in an amount of about 0.01% by weight to a large excess, preferably 0.05 to 30% by weight, based on the weight of the starting compound (IA).

The reaction temperature and time are determined depending upon the solvent used. When a non-polar solvent such as benzene or chloroform is used, the reaction is generally carried out by heating the reaction system to a temperature near the boiling point of the solvent, and, while the water formed by the reaction is being separated as an azeotrope, the reaction is continued until a theoretical amount of water is separated. When a solvent which is quite miscible with water such as ethanol, pyridine or dioxane is used, the reaction can be performed usually at room temperature to about 120° C., preferably 30° to 60° C., for about 30 minutes to about 24 hours, generally 30 minutes to 3 hours, without separating the water formed by the reaction.

The amount of the active methylene compound of the general formula (II) used in the above dehydrocondensation reaction is at least about 1 equivalent, preferably 1 to 2 equivalents, based on the formyl groups of the starting compound (IA).

(E) Process (5)

Compounds of the general formula (I) in which one or both of $R^2$ and $R^3$ are hydroxyl groups (to be referred to hereinafter as compounds (IF)) can be easily prepared by reacting compounds (IA) with peroxides in an inert solvent.

Examples of suitable inert solvents which can be used are aqueous solutions of alkalis such as sodium hydroxide and potassium hydroxide, water, pyridine, methanol, ethanol, acetic acid, propionic acid, chloroform, methylene chloride, methyl acetate, ethyl acetate, benzene and toluene. Suitable peroxides which can be used are organic or inorganic peroxides such as hydrogen peroxide, peracetic acid, trifluoroperacetic acid, m- chloroperbenzoic acid, perbenzoic acid, and perfumaric acid.

The reaction temperature is usually about 0° to about 100° C., preferably 0° to 50° C., and the reaction is completed by stirring the reaction system for about 1 to about 24 hours. The amount of the peroxide is at least about 2 mols, preferably 2 to 3 mols, per mol of the starting compound (IA). After the reaction, a suitable neutralizing agent is added, and the mixture is concentrated under reduced pressure. The residue is added to ice water, and the precipitated crude crystals are collected by filtration, washed with water, and dried. The dried crude crystals are dissolved in a suitable solvent such as chloroform, and separated by column chromatography. The desired compound (IF) is obtained usually as a methanol-eluted fraction.

(F) Process (6)

Compounds of the general formula (I) in which both $R^2$ and $R^3$ represent lower alkanoyloxymethyl groups (to be referred to hereinafter as compounds (IG)) can be prepared by acylating the compounds (IC) obtained by Process (2) described herinabove.

Lower alkanoic acids such as acetic acid, propionic acid, butyric acid, isobutyric acid, etc., the acid anhydrides thereof or the acid halides thereof such a acetyl chloride, propionyl bromide, butyryl bromide, isobutyl bromide, etc., for example, can be used as an acylating agent in the above reaction. Lower alkanoic acid anhydrides and acid halides are preferred. The acylation reaction can be carried out in the absence of a solvent or in the presence of a conventional inert solvent in the presence of a basic compound. Examples of suitable inert solvents which can be used are aromatic hydrocarbons such as benzene and toluene, ethers such as diethyl ether, dioxane or tetrahydrofuran, halogenated hydrocarbons such as chloroform and methylene chloride, tertiary amines such as pyridine and triethylamine, dimethyl sulfoxide, and dimethylformamide. Useful basic compounds include, for example, sodium carbonate, potassium carbonate, sodium hydrogen carbonate, and tertiary amines such as pyridine, quinoline, N,N-dimethylaniline or triethylamine. A suitable amount of the basic compound is at least about 1 mol, preferably 1 to 2 mols, per mol of the starting compound (IC) when an acid halide is used as the acylating agent and about 0.01 to 10% by weight, preferably 1 to 5% by weight, based on the weight of the starting compound (IC) when an acid anhydride is used as the acylating agent.

The reaction can be carried out at a temperature of about $-60°$ to about 150° C., preferably 0° to 100° C., and is completed in about 1 to about 20 hours. The amount of the acylating agent is at least about 1 equivalent, usually 1 to 10 equivalents, based on the hydroxyl groups of the starting compound (IC).

When a compound of the formula (IF) in which not only $R^2$ and $R^3$ but also at least one of $-OR^1$, $R^4$ and $R^6$ represent a hydroxyl group is used as the starting material in the above acylation reaction, the other hydroxyl group or groups are sometimes acylated also depending upon the acylation conditions, especially depending upon the choice of the reaction temperature or the amount of the acylating agent. When it is desired to selectively acylate $R^2$ and $R^3$ in the case of using such a starting compound, the other hydroxyl group of groups can be protected using suitable conventional techniques prior to the reaction, and after the acylation of $R^2$ and $R^3$, the protective groups are removed.

(G) Process (7)

Compounds of the formulae (IA) to (IG) obtained using the above-described procedures in which $R^1$ represents a lower alkyl group can be prepared by reacting the corresponding compounds in which $R^1$ is a hydrogen atom, with known alkylating agents.

Examples of suitable alkylating agents which can be used include alkyl halides such as methyl iodide, ethyl bromide, propyl bromide, isopropyl bromide, butyl iodide and tert-butyl bromide, dialkyl sulfates such as dimethyl sulfate or diethyl sulfate, and diazoalkanes such as diazomethane or diazoethane.

The alkylation reaction can be carried out at room temperature to about 100° C., preferably 30° to 70° C., in a conventional inert solvent, for example, a ketone such as acetone or methyl ethyl ketone, an ether such as tetrahydrofuran or dioxane, or a lower alcohol such as methanol or ethanol, in the presence of a basic compound such as potassium carbonate, sodium carbonate, sodium hydroxide or potassium hydroxide in an amount of about 1 to about 10 mols, preferably 1 to 2 mols, per mol of the alkylating agent. The reaction is completed usually in about 1 to about 8 hours. The amount of the alkylating agent used is at least about 1 mol, usually 1 to 5 mols, per mol of the starting material (IA) to (IG). When diazoalkanes are used as the alkylating agent, the use of the basic compound can be omitted.

(H) Process (8)

Compounds of the formulae (IA) to (IG) in which $R^1$ is a lower alkanoyl group can be obtained using a known aculation reaction of the corresponding compounds in which $R^1$ is a hydrogen atom.

The acylation reaction can be performed in accordance with Process (6) described hereinabove.

If compounds of the general formula (I) which have a hydroxyl group at positions other than the 4'-position are used as a starting material, such a hydroxyl group is likely to be acylated also under the acylating conditions described above for Process (6). Hence, in acylating such starting compounds, the hydroxy group at a position other than the 4'-position is preferably protected in a conventional manner with a suitable protective group.

(I) Process (9)

Compounds of the general formulae (IA) to (IG) in which $R^4$ and $R^6$ are lower alkanoyloxy groups can be prepared by acylating the corresponding compounds in which $R^4$ and $R^6$ are hydroxyl groups. In this reaction, too, the same acylation conditions, protection and subsequent removal of the protective groups for other functional groups as described in Process (6) above can be used.

(J) Process (10)

Compounds of the general formulae (IA) to (IG) in which $R^4$ and $R^6$ are lower alkylidenedioxy groups can be prepared by reacting the corresponding compounds in which $R^4$ and $R^6$ are hydroxyl groups, with aldehydes or ketones of the general formula (III):

wherein $R^{10}$ and $R^{11}$, which may be the same or different, each represents a hydrogen atom or a lower alkyl group, or with acetals or ketals of the following general formula (IV):

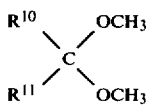

(IV)

wherein $R^{10}$ and $R^{11}$, which may be the same or different, each is as defined hereinabove.

This reaction can be carried out in the presence of a catalyst, in the absence of a solvent, or in the presence of a suitable solvent. Examples of suitable solvents which can be used are aromatic hydrocarbons such as benzene and toluene, ethers such as diethyl ether and dioxane, halogenated hydrocarbons such as chloroform and methylene chloride, and ketones such as acetone and methyl ethyl ketone. Examples of suitable catalysts which can be used include hydrogen halides such as hydrogen chloride and hydrogen bromide, sulfuric acid, Lewis acids, anhydrous aluminum chloride, anhydrous zinc chloride and boron trifluoride, and p-toluenesulfonic acid. A suitable amount of the catalyst ranges from about 0.1 to about 20% by weight, preferably 5 to 10% by weight, based on the weight of the starting compound (IA) to (IG). The compounds of the general formulae (III) and (IV) used for the reaction are usually employed in an excess amount to the compounds of the general formulae (IA) to (IG), since they also act as a solvent. A suitable reaction temperature is about $-30°$ C. to about 70° C., preferably 0° C. to room temperature. Under these conditions, the reaction is completed in about 30 minutes to about 6 hours.

(K) Process (11)

Compounds of the general formulae (IA) to (IG) in which $R^4$ and $R^5$, taken together, represent an oxo group ($=O$) can be obtained by oxidizing the corresponding compounds in which $R^4$ is a hydroxyl group and $R^5$ is a hydrogen atom.

The oxidation reaction can be carried out by using various known oxidizing agents which are used to oxidize secondary alcohols to an oxo group. Examples of suitable oxidizing agents which can be used are chromic acid, bichromic acid, salts of these acids with metals such as sodium or potassium, nitric acid, halogens such as bromine or chlorine, Oppenauer oxidizing agent, and Jones reagent.

The reaction is carried out preferably in a suitable solvent. Examples of suitable solvents are water, alcohols such as methanol and ethanol, ethers such as dioxane, tetrahydrofuran and diethyl ether, ketones such as acetone and methyl ethyl ketone, organic acids such as acetic acid and propionic acid, esters such as ethyl acetate, aromatic hydrocarbons such as benzene and chlorobenzene, halogenated hydrocarbons such as dichloromethane and dichloroethane, dimethylformamide, dimethyl sulfoxide, and pyridine.

The amount of the oxidizing agent can be selected appropriately within a broad range. Usually, an excess of the oxidizing agent is used.

The reaction can be carried out at about $-10°$ C. to about 100° C., preferably 0° C. to room temperature, for about 30 minutes to about 6 hours. If in the oxidation reaction described above, starting compounds having groups which tend to be affected by the oxidation reaction, such as a formyl or hydroxyl group, are used, it is desirable to protect these groups with suitable protective groups in a conventional manner in the same manner as in Process (6) described above. Removal of the protective groups after the reaction can be easily performed in a conventional manner.

The sesquiterpene derivatives expressed by the general formula (I) in this invention can be obtained using one or more of Process (1) to Process (11) described above in suitable sequences, and, if desired, by protecting reactive sites followed by protective group removal and using various separtion and purification procedures.

Of the sesquiterpene derivatives of the formula (I) of this invention, those containing acidic groups, that is, a phenolic hydroxyl group and/or carboxyl group, can be reacted with basic compounds to easily form the salts thereof. The present invention also includes the salts of the sesquiterpene derivatives of the general formula (I).

Examples of basic compounds that can be used in the production of the salts of the sesquiterpene derivatives of the general formula (I) include the hydroxides and carbonates of alkali metals and alkaline earth metals, such as sodium hydroxide, potassium hydroxide, calcium hydroxide, sodium carbonate, potassium carbonate, and sodium hydrogen carbonate. Organic amines, such as methylamine, ethylamine, isopropylamine, morpholine, piperazine, piperidine, and 3,4-dimethoxyphenethylamine, can also be used as the basic compounds.

Salt formation using basic compounds can be performed easily in a suitable solvent using conventional salt-formation techniques. Examples of suitable solvents which can be used are water, lower alcohols such as methanol, ethanol and propanol, ethers such as dioxane and tetrahydrofuran, acetone, benzene, ethyl acetate, dimethyl sulfoxide, dimethylformamide, methylene chloride, and chloroform. Salt formation can be carried out at room temperature to about 100° C., preferably room temperature to 50° C., for about 5 minutes to about 6 hours usually open to the atmosphere or under oxygen-free conditions, preferably in an atmosphere of an inert gas such as nitrogen or argon. The amount of the basic compound used is not particularly restricted, but usually, a suitable amount is at least about 1 equivalent, preferably 1 to 2 equivalents, based on the acidic groups of the starting compound (I).

After the reactions described above have been completed, the desired final compound can be easily separated and purified using known conventional separation procedures. For example, distillation of solvent, solvent extraction, precipitation, recrystallization, column chromatography, and preparative chromatography, for example, can be employed as separation procedures.

III. THERAPEUTIC AGENTS

The resulting sesquiterpene derivatives of the general formula (I) and the salts thereof of the present invention are useful as an agent for treating nephritis and when used as a nephritis treating agent, are formulated into pharmaceutical compositions together with ordinary pharmaceutically acceptable carriers. Suitable carriers which can be used are, for example, diluents or excipients such as fillers, extenders, binders, wetting agents, distintegrants, surface active agents and lubricants which are usually employed to prepare such drugs depending on the dosage form.

Various dosage forms of the therapeutic agents as a nuphritis treating agent can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the sesquiterpene derivative of the general formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonte, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween, sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

In molding the pharmaceutical composition into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and distintegrants such as laminaria and agar. The tablets, if desired, can be coated, and made into sugar-coated tablets, gelatin-coated tablets, enteric-coated tablets, film-coated tablets, or tablets coated with two or more layers.

In molding the pharmaceutical composition into a suppository form, a wide variety of carriers known in the art can be used. Examples of suitable carriers include polyethylene glycol, cacao butter, higher alcohols, esters of higher alcohols, gelatin, and semi-synthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The amount of the compound of the general formula (I) and the pharmaceutically acceptable salts thereof of this invention as an active ingredient to be incorporated into a pharmaceutical composition useful as a nephritis treating agent is not particularly limited, and can vary over a wide range. A suitable therapeutically effective amount of the compound of the general formula (I) and the pharmaceutically acceptable salts thereof of this invention is usually about 1 to about 70% by weight, preferably 5 to 50% by weight, based on the entire composition.

There is no particular restriction on the manner of using the therapeutic agent as a nephritis treating agent, and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be singly administered intramuscularly, intracutaneously, subcutaneously, or intraperitoneally. The suppository is administered intrarectally.

The dosage of the nephritis treating agent is suitably selected according to the purpose of use, the symptoms, etc. Usually, a preferred dosage of the compound of this invention is about 0.5 to 20 mg/kg of body weight per day in single or multiple doses.

The compounds of this invention have anticomplementary activities, and are useful also as therapeutic agents for autoimmune diseases, collagen diseases, and rheumatic diseases, each of which involves a complement system.

The results of tests on the pharmacological effects of the compounds of this invention of the general formula (I) and the pharmaceutically acceptable salts thereof are shown below.

(1) Compounds Tested

Representative compounds of this invention as described hereinbefore and as shown in Table 1 below were tested. The compounds are described further by reference to the general formula (I) with the various substituents thereof also being shown in Table 1 below, i.e.,

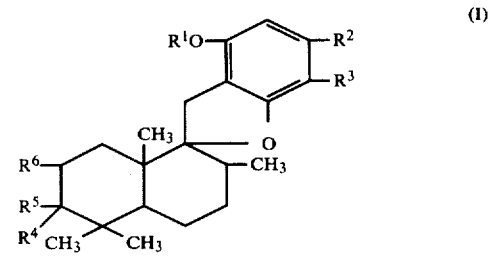

wherein in the compounds shown in Table 1 below, $R^4=-OH$, $R^5=-H$ and $R^6=-OH$.

TABLE 1

| Compound No. | $R^1$ | $R^2$ | $R^3$ |
|---|---|---|---|
| (1) | —H | —CHO | —CHO |
| (67) | —Na | —CHO | —COONa |
| (2) | —H | —OH | —OH |

TABLE 1-continued

| Compound No. | R¹ | R² | R³ |
|---|---|---|---|
| (3) | —H | —CH=C(CN)(CN) | —CH=C(CN)(CN) |
| (4) | —H | —CH=C(CN)(COOC₂H₅) | —CH=C(CN)(COOC₂H₅) |
| (6) | —H | —CH=C(CN)(COOH) | —CH=C(CN)(COOH) |
| (7) | —H | —CH=CHCOOH | —CH=CHCOOH |
| (8) | —H | —CH₂OH | —COOH |
| (11) | —H | —CH₂OH | —CH₂OH |
| (12) | —CH₃ | —CH₂OH | —CH₂OH |

Compound No. (25) has the following structural formula:

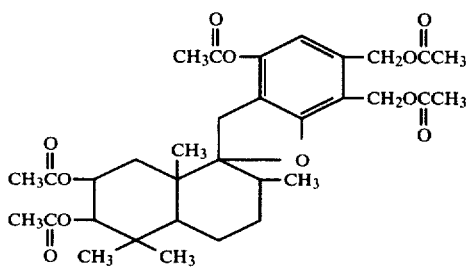

Compound No. (62) has the following structural formula:

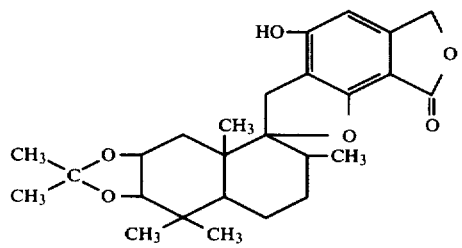

(2) Anti-Complement Activity

The anti-complement activity was measured and confirmed by the testing method described in Meneki Kagaku (Immuno-Chemistry), Yuichi Yamamura et al., Ed. pages 830–834, Asakura Shoten, Tokyo, Japan (1973). Specifically, a test tube was charged with 0.5 ml of an aqueous dispersion of each of the test compounds, 0.5 ml of sensitized erythrocytes (EA) containing $1 \times 10^8$ cells/ml, 1 ml of a 5-fold diluted solution of a Veronal buffer solution containing gelatin, Ca++ and Mg++ (GVB++), and 0.5 ml of complement serum (guinea pig complement) diluted to 150 times with the GVB++. The mixture was maintained hot at 37° C. for 60 minutes. Then, 5 ml of an ice-cold physiological saline solution was added thereto, and the mixture was centrifuged. The absorbance of the supernatant separated was measured at OD₄₁₃, and the extent the test compound inhibited the hemolysis of the sensitized erythrocytes was determined. The 50% hemolysis inhibitory activity value (γ/ml) measured by the above method is shown in Table 2 below for each test compound.

(3) Acute Toxicity

The LD₅₀ values (mg/kg) of the test compounds on intravenous administration to mice were measured, and the results obtained are also shown in Table 2 below.

TABLE 2

| Compound No. | Anti-Complement Activity Value (γ/ml) | LD₅₀ Value (mg/kg) |
|---|---|---|
| (1) | 10 | 40 |
| (67) | 60 | 500 |
| (2) | 80 | 150 |
| (3) | 40 | 200 |
| (4) | 80 | 200 |
| (6) | 40 | 250 |
| (7) | 80 | 150 |
| (8) | 125 | — |
| (11) | 500 | — |
| (12) | 250 | — |
| (25) | 600 | — |
| (62) | 450 | — |
| Chlorophyllin | 40 | — |

(4) Therapeutic Effect on Nephrotoxin-Type Nephritis

Rat nephrotoxin ("NT" for brevity) was obtained as described below. Rat kidney cortex was homogenized with an equal quantity of physiological saline. The homogenized mixture was mixed with Freund's complete adjuvant (a product of Difco Company) in a volume ratio of 1:1. Two milliliters of the resulting mixture was intramuscularly injected into a rabbit (body weight 3,100 g) to immunize the rabbit. A month and a half later, blood was taken from the heart of the rabbit and serum was obtained. The resulting serum was inactivated at 56° C. for 30 minutes, then salted out with a 40% saturated aqueous solution of ammonium sulfate, and fractionated. The γ-globulin (IgG) fraction was collected to obtain NT.

The evaluation was carried out using male Wistar rats with a body weight of 150 to 160 g with three replications for each test compound. The test compound was intraperitoneally administered once every 24 hours for seven days. One hour after the administration of the test compound on the third day, the NT was applied. The NT was intravenously injected in an amount of 1 ml at a tail vein of each rat. Chlorophyllin (CP) was used as a comparison compound, and physiological saline solution was used as a control.

The proteinuria level (total amount excreted into the urine over a 24 hour period) was measured using turbidometry employing bovine serum albumin as a control by means of sulfosalicylic acid.

The results obtained are shown in Table 3 below.

TABLE 3

| Compound No. | Dosage (mg per rat) | Replication Number | Day Number* | | | |
|---|---|---|---|---|---|---|
| | | | 1 | 4 | 7 | 10 |
| Compound No. (1) | 3 | 1 | 2.5** | 1.5 | 0.8 | 8 |
| | | 2 | 4.3 | 2.1 | 1.8 | 10 |
| | | 3 | 1.7 | 1.1 | 0.9 | 7 |
| | | Average | 2.8 | 1.6 | 1.2 | 8 |
| Compound | 5 | 1 | 2.7 | 1.8 | 0.7 | 9 |
| | | 2 | 4.1 | 2.0 | 1.5 | 12 |

TABLE 3-continued

| Compound No. | Dosage (mg per rat) | Replication Number | Day Number* 1 | 4 | 7 | 10 |
|---|---|---|---|---|---|---|
| No. (67) | | 3 | 2.3 | 1.3 | 1.2 | 7 |
| | | Average | 3.0 | 1.7 | 1.1 | 9 |
| Compound | 5 | 1 | 2.1 | 1.9 | 0.8 | 13 |
| | | 2 | 1.5 | 1.2 | 0.9 | 7 |
| No. (6) | | 3 | 3.7 | 2.3 | 1.4 | 9 |
| | | Average | 2.5 | 1.8 | 1.0 | 10 |
| Chlorophyllin | | 1 | 2.4 | 1.5 | 0.9 | 9 |
| | 5 | 2 | 4.4 | 2.6 | 1.7 | 8 |
| (comparison) | | 3 | 3.2 | 2.1 | 3.5 | 6 |
| | | Average | 3.4 | 2.1 | 2.0 | 8 |
| | | 1 | 13 | 16 | 21 | 29 |
| | | 2 | 19 | 23 | 25 | 35 |
| (control) | — | | | | | |
| | | 3 | 11 | 18 | 24 | 40 |
| | | Average | 14 | 19 | 23 | 35 |

*The day number in Table 3 is counted from the time of administration of the test compound which was 1 hour before the application of the NT.
**The amount of proteinurea is given in units of mg/day.

The proteinurea level in a healthy rat is 0.5 to 5 mg/day. When the proteinurea level exceeds this range, especially when the proteinurea level is more than 10 mg/day, it may safely be said that nephritis has occurred. As can be seen from the results in Table 3, nephritis occurred in the control lot, and in the case of the compounds of the present invention and CP, the amount of proteinurea from the time of administration of NT to 10 days after administration is substantially the same as that of a healthy rat. Thus the administration of the compounds of this invention can be seen to inhibit primary and secondary immune reactions.

When the same test was conducted on Compounds Nos. 3 to 5, 7, 8, 11, 12, 25 and 62 of the invention, all of these compounds were found to inhibit the primary reaction of nephrotoxintype nephritis.

(5) Therapeutic Effects on Heymann-type Nephritis

Male Wistar rats with a body weight of 180 to 200 g were used in the test. Rat kidney cortex was extracted, and homogenized with an equal quantity by volume of a physiological saline solution. The homogenate was centrifuged at 1500 G for 1 hour. The supernatant liquid was purified in accordance with the method of T. S. Edgington et al., Journal of Experimental Medicine, 127, 555 (1968), and mixed with Freund's complete adjuvant 37 Ra (a product of Difco Company) in volume ratio of 0.4:1. The resulting mixture was injected intraperitoneally into isologous rats in an amount of 0.5 ml per rat. Thereafter, the same amount of the adjuvant was administered every 2 weeks until the proteinurea level exceeded 100 mg/day. (This period was about 6 to 8 weeks.)

Each of the test compounds indicated in Table 4 below was intraperitoneally administered to the rats affected with Heymann-type nephritis (with a body weight of 300 to 350 g) once a day for 7 days, and then the amount of proteinurea (mg/day) was measured in the same manner as described above. CP was used as a comparison compound, and physiological saline solution was used as a control. Three replications were conducted for each test compound. The results obtained are shown in Table 4 below.

TABLE 4

| Compound No. | Dosage (mg per rat) | Replication Number | Before Administration | Day Number 1 | 4 | 7 | 14 | 21 |
|---|---|---|---|---|---|---|---|---|
| Compound No. (1) | 3 | 1 | 95 | 90 | 47 | 17 | 9 | 10 |
| | | 2 | 132 | 125 | 65 | 35 | 15 | 12 |
| | | 3 | 121 | 120 | 70 | 27 | 10 | 9 |
| | | Average | 116 | 111 | 61 | 26 | 11 | 10 |
| Compound No. (67) | 5 | 1 | 117 | 109 | 59 | 23 | 13 | 9 |
| | | 2 | 132 | 127 | 67 | 41 | 17 | 13 |
| | | 3 | 105 | 114 | 51 | 25 | 11 | 12 |
| | | Average | 118 | 117 | 59 | 30 | 14 | 11 |
| Compound No. (6) | 5 | 1 | 98 | 113 | 48 | 36 | 18 | 8 |
| | | 2 | 127 | 121 | 63 | 47 | 21 | 15 |
| | | 3 | 139 | 116 | 57 | 29 | 13 | 14 |
| | | Average | 121 | 116 | 56 | 37 | 17 | 12 |
| Chlorophyllin (comparison) | 5 | 1 | 123 | 116 | 72 | 32 | 16 | 10 |
| | | 2 | 117 | 108 | 63 | 29 | 12 | 8 |
| | | 3 | 129 | 121 | 52 | 22 | 15 | 13 |
| | | Average | 123 | 115 | 62 | 28 | 14 | 10 |
| (control) | — | 1 | 135 | 127 | 132 | 135 | 114 | 126 |
| | | 2 | 121 | 105 | 121 | 103 | 105 | 109 |
| | | 3 | 137 | 117 | 135 | 121 | 109 | 132 |
| | | Average | 131 | 116 | 129 | 119 | 109 | 122 |

Two to three weeks after the beginning of the testing, the body weights of the rats increased to 400 to 500 g, and normal proteinurea levels are believed to be 5 to 15 mg/day. As can be seen from the results in Table 4, the compounds of the present invention can cure Heymann-type nephritis.

When the same test was conducted on Compounds Nos. 3 to 5, 7, 8, 11, 12, 25 and 62 of the invention, a substantial activity of curing Heymann-type nephritis was found for these compounds as well.

IV. EXAMPLES

To illustrate the present invention in more detail, the production of the compounds of this invention of the general formula [I] is described in the following Examples, and the production of nephritis treating agents containing the compounds of the invention of the general formula I as an active ingredient are described in the following Reference Examples. Unless otherwise indicated herein, all parts, percents, ratios and the like are by weight and the term room temperature as used herein means 15° to 25° C.

EXAMPLE 1

A 500 ml Sakaguchi flask was charged with 100 ml of a culture medium of the following formulation, and Stachybotrys sp. K-76 was cultivated at 28° C. and a pH of 6 for 4 days with shaking.

| Formulation of Culture Medium | (%) |
|---|---|
| Glycerol | 0.5 |
| Starch | 1.0 |

-continued

| Formulation of Culture Medium | |
|---|---|
| | (%) |
| Lactose | 0.2 |
| Soybean Powder | 0.5 |
| Yeast Extract | 0.1 |
| Malt Extract | 0.2 |
| CaCO$_3$ | 0.3 |
| MgSO$_4$ | 0.05 |

A 30-liter jar fermentor was charged with 20 liters of a culture medium of the above formulation, and one flask of the resulting seed culture was cultivated in the culture medium at 28° C. for 5 days with stirring at 400 rpm at an aeration rate of 1 liter per liter of the culture medium per minute. The resulting culture broth was centrifuged at a speed of 8000 rpm to remove the microbial cells. To the supernatant liquid was added 5 liters of methanol, and the mixture was stirred and then allowed to stand for 3 hours. The mixture was centrifuged and the solid material was removed. The supernatant was extracted with an equal quantity by volume of ethyl acetate. The solvent of the ethyl acetate layer was distilled off under reduced pressure. The residue was dissolved in methanol, and passed through a column of activated carbon. The eluate was concentrated to dryness under reduced pressure. The dried mass was dissolved in a mixture of chloroform and ethyl acetate (1:1, v/v) and gel-filtered through a column of Sephadex LH-20. The filtrate was subjected to thin-layer chromatography [using a mixture of ethyl acetate, chloroform and acetic acid (volume ratio of 50:50:2) as a developing solvent], and a fraction having an anti-complement activity corresponding to Rf=0.34 was collected. Alternatively the filtrate was subjected to thin-layer chromatography [using a mixture of benzene, butanol and acetic acid (volume ratio of 60:15:5) as a developing solvent], and a fraction having an anti-complement activity corresponding to Rf=0.58 was collected. Evaporation of the solvent from the fraction afforded 2.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran), a light yellow weakly acidic substance having an anti-complement activity. Production of this compound was confirmed by the following physicochemical characteristics.

(1) $[\alpha]_D^{20} = -48°$ (C=2.5, methanol)

(2) Elemental Analysis Values for $C_{23}H_{30}O_6$: Calculated (%): C, 68.64; H, 7.51. Found (%): C, 68.58; H, 7.55.

(3) Ultraviolet Absorption Spectral (UV) Analysis $\lambda_{max}^{ethanol}$ = 246 nm ($\epsilon$ = 16474)
 = 307 nm ($\epsilon$ = 6659)

(4) Nuclear Magnetic Resonance Spectral (NMR) Analysis

Figure 5:
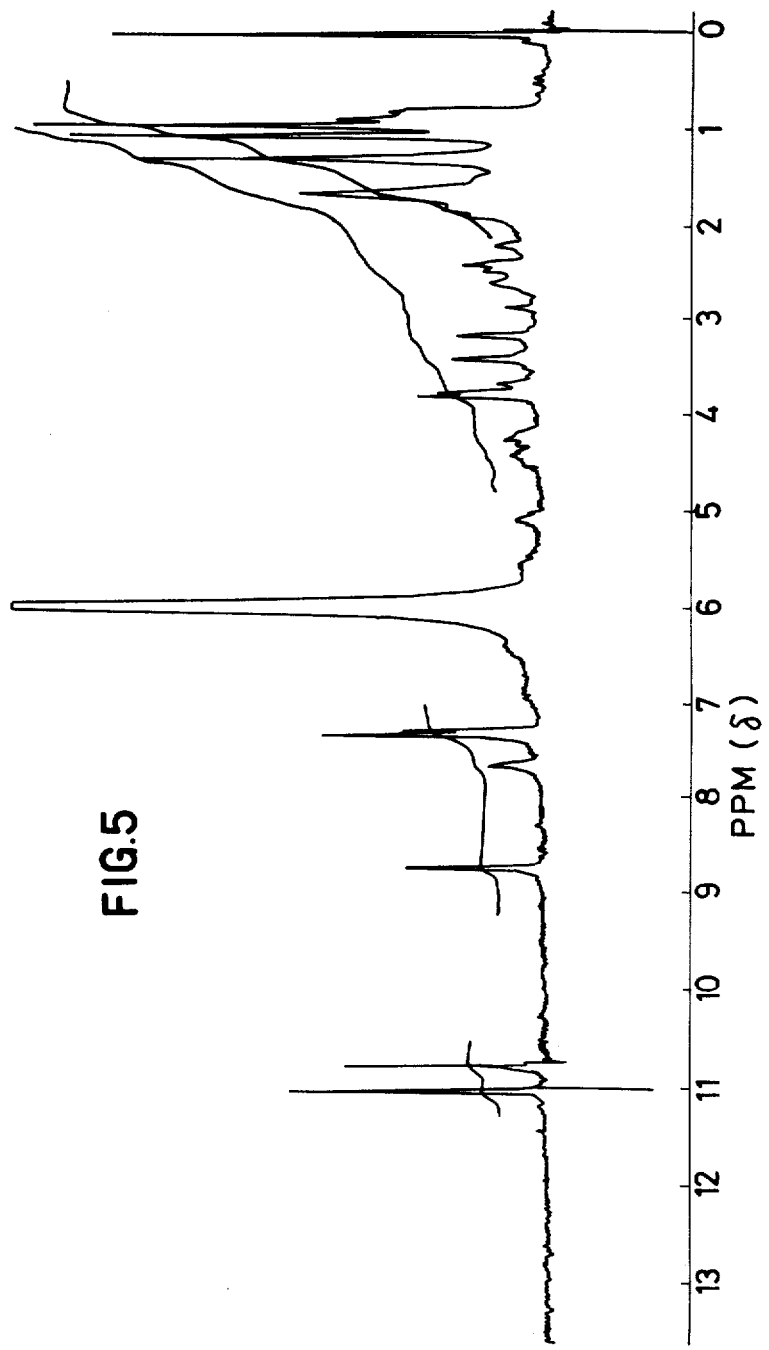
FIG. 5 is a nuclear magnetic resonance spectrum of the compound of the formula (Ia) obtained in Example 1 of the present invention.

NMR analysis was conducted using pyridine-d$_5$ [sodium 2,2-dimethyl-2-silapentane-5-sulfonate (DSS) as an internal standard] as a solvent. The NMR chart obtained is shown in FIG. 5. The NMR measurement conditions were as follows:
Spectral Amplitude: 4×100
Filter: 0.1 sec.
RF Output: 0.5 mG
Sweep Time: 5 minutes
Sweep Width: 10 ppm
Sweep End: 0 ppm

EXAMPLE 2

A 500 ml Sakaguchi flask was charged with 100 ml of a culture medium having the following formulation, and *Stachybotrys chartarum* IFO 5369, a known strain, was cultivated in the medium at 28° C. for 4 days at a pH of 6 with shaking.

| Formulation of Culture Medium | |
|---|---|
| | (%) |
| Glycerol | 0.5 |
| Starch | 1.0 |
| Lactose | 0.2 |
| Soybean Powder | 0.5 |
| Yeast Extract | 0.1 |
| Malt Extract | 0.2 |
| CaCO$_3$ | 0.3 |
| MgSO$_4$ | 0.05 |

A 30-liter jar fermentor was charged with 20 liters of a culture medium having the above formulation, and two flasks of the resulting seed culture were cultivated at 28° C. for 5 days with stirring at a speed of 30 rpm at an aeration rate of 1 liter per liter of the medium per minute. The resulting culture broth was centrifuged at a speed of 8000 rpm to remove the microbial cells. To the supernatant liquid was added 5 liters of methanol, and the mixture was stirred and allowed to stand for 3 hours. The mixture was centrifuged and the solid material was removed. The supernatant was extracted with an equal quantity by volume of ethyl acetate. The solvent of the ethyl acetate layer was removed under reduced pressure to concentrate to dryness. The residue was dissolved in methanol, and passed through a column of activated carbon. The eluate was concentrated to dryness under reduced pressure, dissolved in a mixture of chloroform and ethyl acetate (1:1, v/v), and gel-filtered through a column of Sephadex LH-20. Fractions having active peaks corresponding to the thin-layer chromatography Rf values described in Example 1 were collected. Evaporation of the solvent afforded 2.2 g of (6,7-dihydroxy-2,5,5,8a- tetramethyl-1,2,3,4,4a,5,6,7,8,8a-decahydronaphthalene-1-spiro-2'-(6',7'-diformyl-4'-hydroxy-2',3'-dihydrobenzofuran), a light yellow weakly acidic substance having an anti-complement activity. This compound had the same physicochemical characteristics as described in Example 1, and production of this compound was confirmed from these characteristics.

EXAMPLE 3

Stachybotrys sp. T-789 was cultivated and purified in the same manner as in Example 1 except that a culture medium of the following formulation adjusted to a pH of 7.5 was used and the cultivation temperature was maintained at 32° C.

| Formulation of Culture Medium | |
|---|---|
| | (%) |
| Glycerol | 0.5 |
| Glucose | 1.2 |
| Corn Steep Liquor | 0.5 |
| Dried Yeast | 0.1 |
| Malt Extract | 0.2 |
| MgSO$_4$ | 0.05 |

| Formulation of Culture Medium | |
|---|---|
| | (%) |
| NaCl | 0.3 |

Thus, 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran), a light yellow weakly acidic substance having an anti-complement acitivity was obtained. The physicochemical properties of this compound agreed with those of the compound isolated and purified in Example 1.

EXAMPLE 4

Stachybotrys sp. T-791 was cultivated and purified in the same manner as in Example 1 except that a culture medium having the following formulation adjusted to a pH of 5.5 was used, and the cultivation temperature was maintained at 25° C.

| Formulation of Culture Medium | |
|---|---|
| | % |
| Gylcerol | 0.5 |
| Starch | 1.0 |
| Sucrose | 0.2 |
| Soybean Powder | 0.5 |
| Peptone | 0.1 |
| Malt Extract | 0.2 |
| MgSO$_4$ | 0.3 |
| HCl | 0.05 |

Thus, 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran), a light yellow weakly acidic substance having an anti-complement activity, was obtained. The physicochemical properties of this compound agreed with those of the compound obtained in Example 1.

EXAMPLE 5

Silver nitrate (2.1 g) was dissolved in 1 ml of water, and 3.5 ml of a 5.8 M aqueous solution of sodium hydroxide was added thereto. The mixture was stirred at room temperature for 20 minutes. Then, a solution of 1.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) obtained as described in Example 1 in 2 ml of ethanol was added thereto. The reaction medium was stirred at room temperature for 1.5 hours, and the pH was adjusted to about 2 with 2 N hydrochloric acid. The reaction mixture was extracted with the same quantity by volume of ethyl acetate, and the solvent in the extract was distilled off under reduced pressure. The residue was purified by silica gel column chromatography [silicagel "Wako C-200", a product of Wako Junyaku Kabushiki Kaisha, chloroform/ethyl acetate/acetic acid (100:50:2 by volume) as an eluent]. A fraction corresponding to Rf=0.37 by thin-layer chromatography [using a mixture of ethyl acetate, chloroform and acetic acid in a volume ratio of 50:50:2 as a developing solvent], or a fraction corresponding to Rf=0.71 in thin-layer chromatography [using a mixture of benzene, butanol and acetic acid in a volume ratio of 60:15:5 as a developing solvent] was collected. Evaporation of the solvent from the fraction afforded 700 mg of 4,6-dihydroxy-8-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene) as light yellow amorphous crystals. The compound had the following physicochemical properties, and production of this compound was confirmed from these properties.

(1) $[\alpha]_D^{20} = -44.8°$ (C=0.9, methanol)

(2) Elemental Analysis Values for $C_{23}H_{30}O_7$: Calculated (%): C, 66.03; H, 7.18. Found (%): C, 65.93; H, 7.21.

Figure 6:
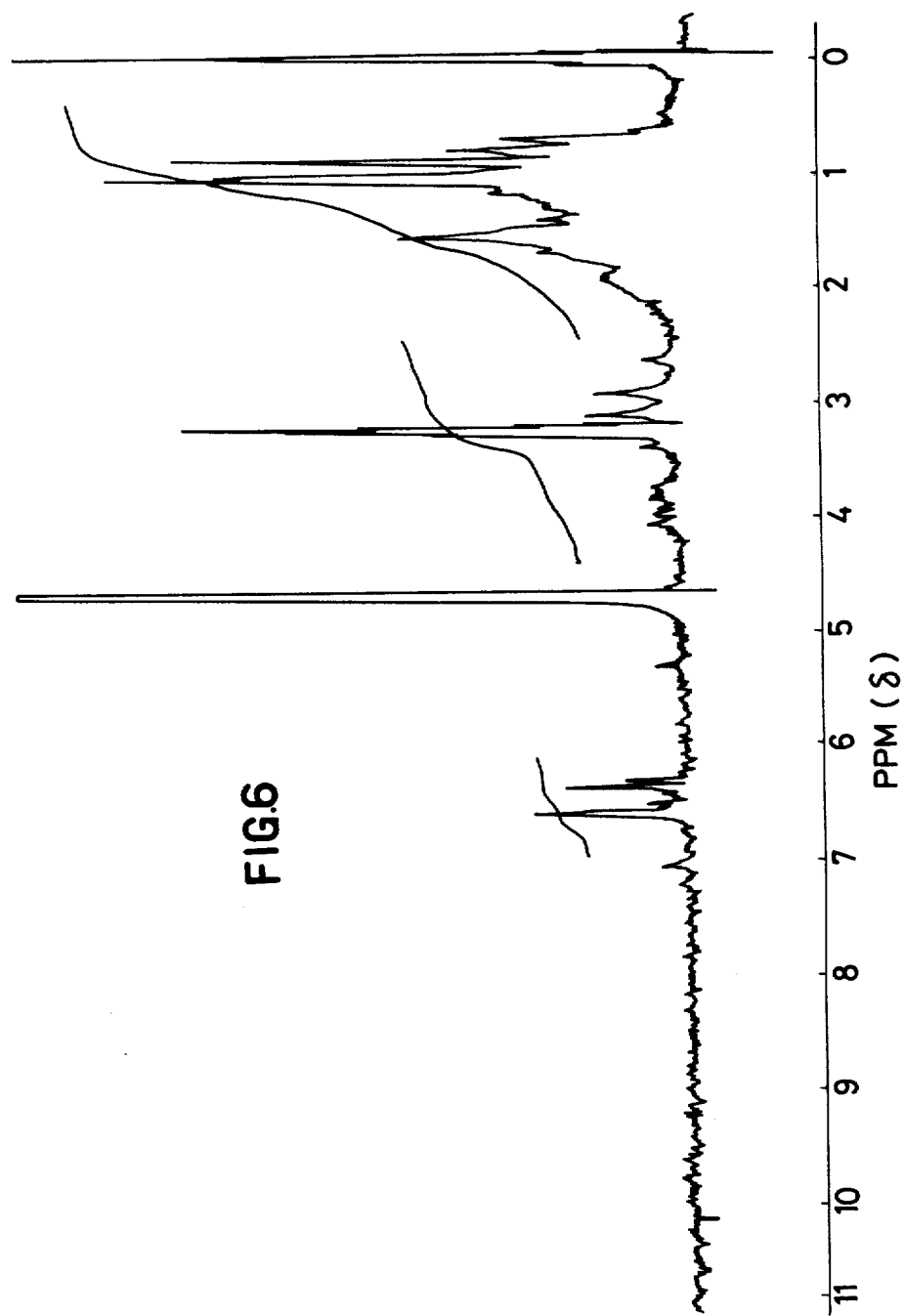
FIGS. 6 to 8 are nuclear magnetic resonance spectra of the compound (Ib) of this invention obtained in Example 5 as measured in three different solvents.

(3) Nuclear Magnetic Resonance Spectral (NMR) Analysis (i) NMR analysis was carried out using CD$_3$OD (DSS) as a solvent, and the NMR chart obtained is shown in FIG. 6.

Figure 7:
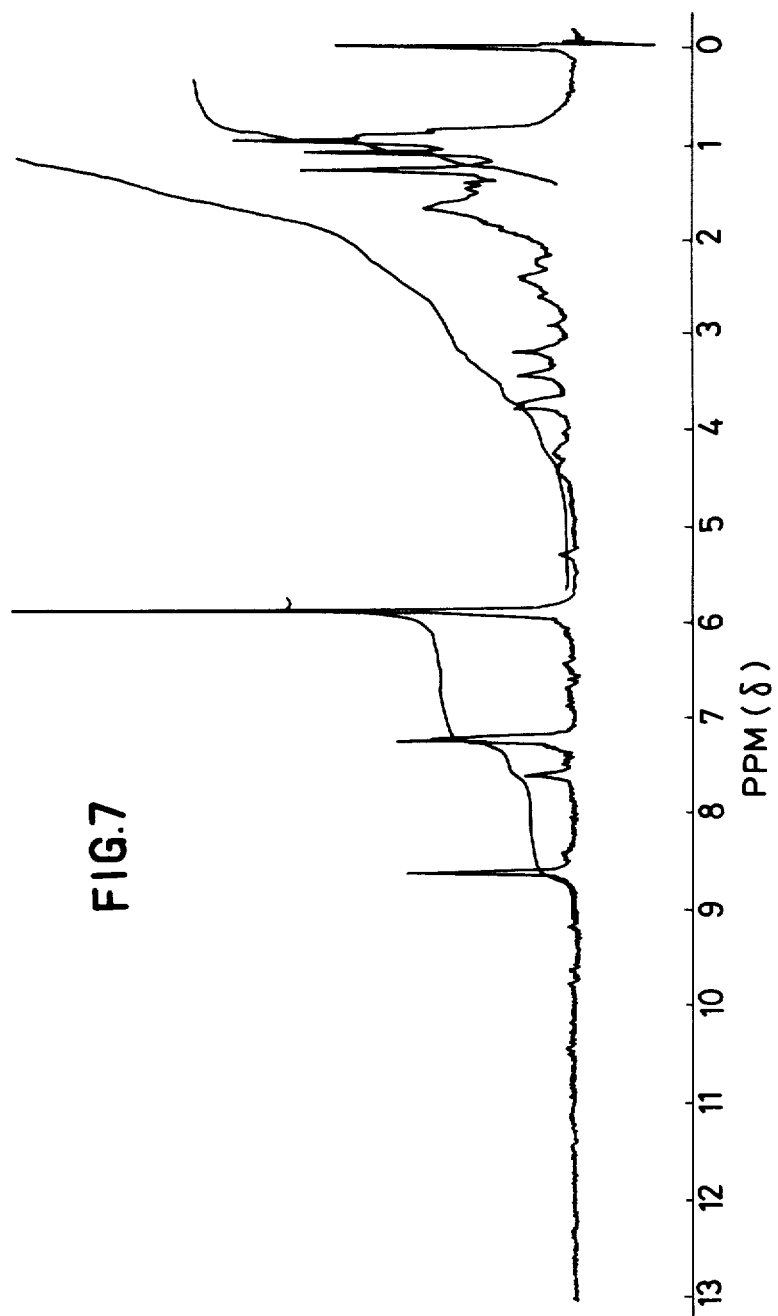

(ii) NMR analysis was conducted using pyridine-d$_6$ (DSS) as a solvent, and the resulting NMR chart is shown in FIG. 7.

(iii) Dimethyl sulfoxide-d$_6$ was used as a solvent, and NMR analysis was conducted 2 hours and 63 hours after dissolution. The NMR chart obtained is shown in FIG. 8 (the NMR charts 2 hours and 63 hours after dissolution agreed with each other).

Figure 8:
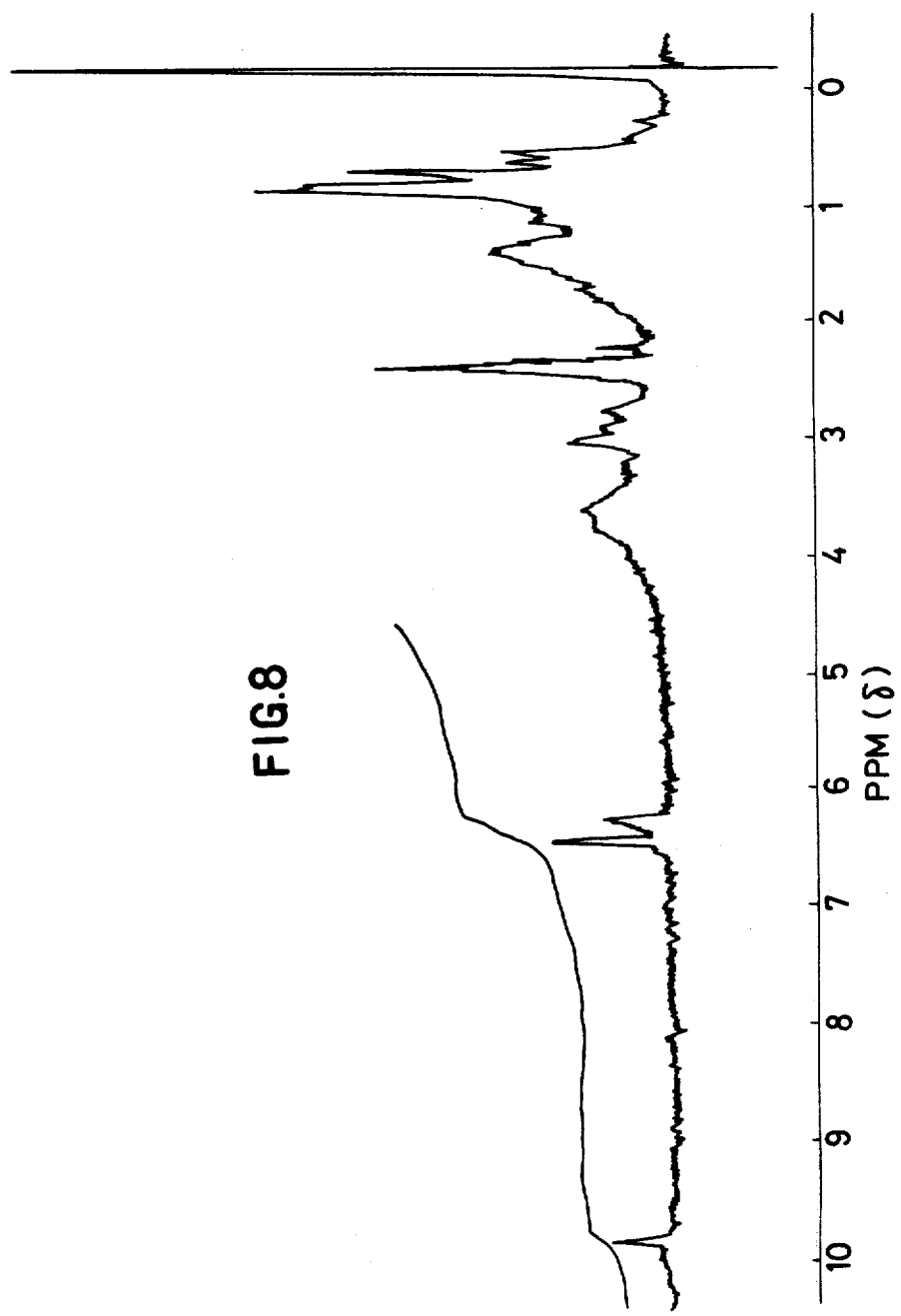

The measurement conditions in obtaining these NMR spectral charts were as follows:

| | FIG. 6 | FIG. 7 | FIG. 8 |
|---|---|---|---|
| Spectral Amplitude | 9 × 100 | 5 × 100 | 8 × 100 |
| Filter | 0.1 sec. | 0.1 sec. | 0.1 sec. |
| RF Output | 0.05 mG | 0.05 mG | 0.05 mG |
| Sweep Time | 5 min. | 5 min. | 5 min. |
| Sweep Width | 10 ppm | 1C ppm | 10 ppm |
| Sweep End | 0 | 0 | 0 |

EXAMPLE 6

Silver oxide (0.64 g) was suspended in a 1 N aqueous solution of sodium hydroxide, and with stirring at room temperature, 1.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) was added. The mixture was stirred at the same temperature for 1 hour, and the precipitate was washed with 10 ml of water 5 times. The washings and the filtrate were combined, and conc. hydrochloric acid (36%) was added to adjust the pH to about 2-3, followed by cooling to 0°-10° C. The crystals which precipitated were collected by filtration, washed with 10 ml of ice water 5 times, and dried. The dried powdery crystals were dissolved in 50 ml of ethyl acetate, and the insoluble matter was separated by filtration. The filtrate was concentrated to a volume of 5 ml under reduced pressure. To the concentrated solution was added 50 ml of ligroin, and the mixture was well stirred and cooled to 0°-10° C. The crystals which precipitated were collected by filtration, washed twice with 20 ml of ligroin, and dried to afford 1.01 g of 4,6-dihydroxy-8-oxo-2,3,6,8-tetrahydrofuro[3,4-g]-benzofuran-2-spiro-1'-(6',7'-dihydroxy-2',5',5',8'a-tetramethyl-1',2',3',4',4'a,5',6',7',8',8'a-decahydronaphthalene). The physicochemical properties of the resulting compound agreed with those of the compound obtained in Example 5.

EXAMPLE 7

1.0 g of 6,7-dihydroxy-2,5,5,8a-tetramethyl-1,2,3,4,4a,5,6,7,8,8a-decahydronaphthalene-1-spiro-2'-

(6',7'-diformyl-4'-hydroxy-2',3'-dihydrobenzofuran) was dissolved in 50 ml of a 10% aqueous solution of sodium hydroxide, and while bubbling air into the solution at 50° C., the solution was stirred for 30 minutes. The solution was acidified with hydrochloric acid to a pH of about 2–3, and the crystals which precipitated were collected by filtration. The crystals were washed with 10 ml of cold water 5 times, and dried. The crystals were dissolved in 50 ml of ethyl acetate, and the insoluble matter was separated by filtration. The filtrate was treated with activated carbon, and concentrated to a volume of 5 ml under reduced pressure. The concentrated solution was added to 50 ml of ligroin with vigorous stirring. The crystals which precipitated were collected by filtration, washed with ligroin, and dried to afford 0.72 g of 4,6-dihydroxy-8-oxo-2,3,6,8-tetrahydrofuro[3,4-g]benzofuran-2-spiro-1'-(6',7'-dihydroxy-2',5',5',8'-a-tetramethyl-1',2',3',4',4'a,5',6',7',8',8'a-decahydronaphthalene). The physicochemical properties of the resulting compound agreed with those of the compound obtained in Example 5.

EXAMPLE 8

1.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) was dissolved in 25 ml of a 1 N aqueous solution of potassium hydroxide, and 50 ml of an aqueous solution of 0.578 g of potassium permanganate was added portionwise thereto with stirring. When the color of the potassium permanganate disappeared, the stirring was stopped. The precipitate was separated by filtration using Celite as a filtration acid. The filtrate was acidified with hydrochloric acid to a pH of about 2–3. The crystals which precipitated were collected by filtration, washed with 10 ml of water three times and then dried. The dried crystals were dissolved in 30 ml of ethyl acetate. The insoluble matter was separated by filtration, and the filtrate was decolorized with activated carbon and concentrated under reduced pressure. To the concentrated solution was added 50 ml of ligroin, and the mixture was stirred. The crystals which precipitated were collected by filtration, washed with ligroin, and dried at 60° C. under reduced pressure to afford 0.9 g of 4,6-dihydroxy-8-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene). The physicochemical properties of the resulting compound agreed with those of the compound obtained in Example 5.

EXAMPLE 9

To 5 ml of a 0.4 N aqueous solution of sodium hydroxide and 5 ml of ethanol was added 418 mg of 4,6-dihydroxy-8-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene). The mixture was stirred at 30° to 40° C. for 30 minutes in a stream of nitrogen. After the reaction, the solvent was distilled off under reduced pressure. The residue was dried, and 10 ml of acetone was added thereto. The acetone-soluble portion was removed by filtration. The resulting crude crystals were recrystallized from water/acetone by adding acetone dropwise to the aqueous solution until crystals precipitated to afford 342 g of disodium 6,7-dihydroxy-2,5,5,8a-tetramethyl-1,2,3,4,4a,5,6,7,8,8a-decahydronaphthalene-1-spiro-2'-(7'-carboxylate-6'-formyl-4'-oxide-2',3'-dihydrobenzofuran) as light yellow amorphous crystals. The resulting compound had the following physicochemical properties, and production of this compound was confirmed from these properties.

(1) $[\alpha]_D^{20} = -44.2°$ (C=1.25, H$_2$O)

(2) Elemental Analysis Values for $C_{23}H_{28}O_7Na_2$: Calculated (%): C, 59.74; H, 6.10. Found (%): C, 59.48; H, 5.91.

(3) Ultraviolet Absorption Spectral (UV) Analysis $$\lambda_{max}^{H_2O} = 252 \text{ nm } (\epsilon = 20500)$$
$$= 330 \text{ nm } (\epsilon = 45900)$$

(4) Nuclear Magnetic Resonance Spectral (NMR) Analysis

Figure 9:
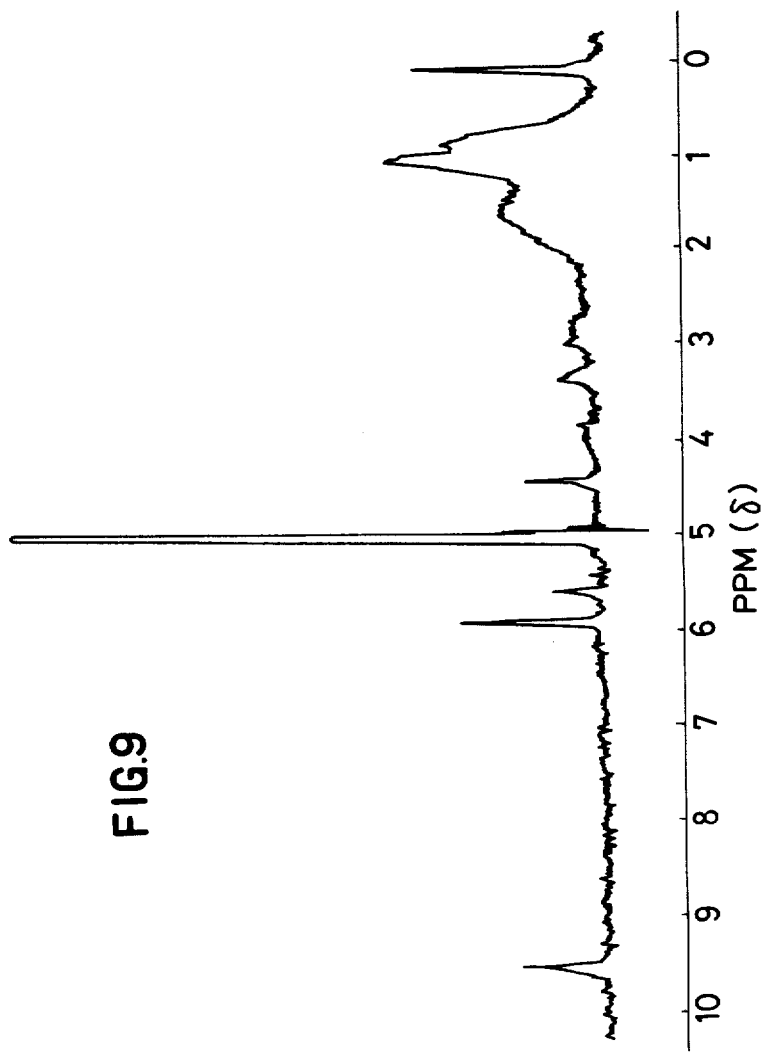
FIG. 9 is a nuclear magnetic resonance spectrum of the compound of this invention obtained in Example 9.

NMR analysis was conducted using D$_2$O (DSS) as a solvent. The resulting NMR chart is shown in FIG. 9. The NMR measurement conditions were as follows:
Spectral Amplitude: 9×100
Filter: 0.1 sec.
RF Output: 0.05 mG
Sweep Time: 5 minutes
Sweep Width: 10 ppm
Sweep End: 0 ppm

EXAMPLE 10

418 mg of 4,6-dihydroxy-8-oxo-2,3,6,8-tetrahydrofuro[3,4-g]benzofuran-2-spiro-1'-(6',7'-dihydroxy-2',5',5',8'a-tetramethyl-1',2',3',4',4'a,5',6',7',8',8'a-decahydronaphthalene) was dissolved in 10 ml of ethyl acetate, and with stirring, 0.33 mole of a 6 N aqueous solution of sodium hydroxide was added thereto. The mixture was stirred at room temperature for 10 minutes to a nitrogen stream. The crystals which precipitated were collected by filtration, washed with 10 ml of ethyl acetate three times, and dried to afford 390 mg of disodium 6,7-dihydroxy-2,5,5,8a-tetramethyl-1,2,3,4,4a,5,6,7,8,8a-decahydronaphthalene-1-spiro-2'-(7'-carboxylate-6'-formyl-4'-oxide-2',3'-dihydrobenzofuran) as light yellow amorphous crystals. The physicochemical properties of the resulting compound agreed with those of the compound obtained in Example 9.

EXAMPLE 11

4.02 g of 6,7-dihydroxy-2,5,5,8a-tetramethyl-1,2,3,4,4a,5,6,7,8,8a-decahydronaphthalene-spiro-2'-(6',7'-diformyl-4'-hydroxy-2',3'-dihydrobenzofuran) was dissolved in a 1 N aqueous solution of sodium hydroxide, and 14.2 g of a 3% aqueous solution of hydrogen peroxide was added thereto. The mixture was stirred at 50° C. for 18 hours. Then, acetic acid was added to adjust the pH of the solution to 3–4. The crystals which precipitated were collected by filtration, washed with water, and dried.

The crude crystals obtained were chromatographed over a column filled with silica gel using a mixture of chloroform and methanol (9:1 by volume) as an eluent. The final eluate was collected, and concentrated to dryness under reduced pressure. Water was added to the residue, and the resulting crystals were collected by filtration, followed by washing with water and drying. Thus, 0.80 g of 6,7-dihydroxy-2,5,5,8a-tetramethyl-1,2,3,4,4a,5,6,7,8,8a-decahydronaphthalene-1-spiro-2'-(4',6',7'-trihydroxy-2',3'-dihydrobenzofuran) was obtained as brown amorphous crystals. When the melting point was measured, it was found this compound gradually decomposed at about 250° C. The physicochemical properties of the resulting product were as follows, and production of this compound was confirmed from these properties.

(1) Melting Point: Gradual decomposition at about 250° C., and no definite melting point observed.

(2) Elemental Analysis Values for $C_{21}H_{30}O_6$: Calculated (%): C, 66.64; H, 7.99. Found (%): C, 66.43; H, 8.13.

(3) Ultraviolet Absorption Spectral (UV) Analysis $$\lambda_{max}^{methanol} = 219 \text{ nm } (\epsilon = 8700)$$
$$= 260 \text{ nm } (\epsilon = 2300)$$

(4) Infrared Absorption Spectral (IR) Analysis The product had the following $\nu_{max}(cm^{-1})$ using the KBr tablet method.

3450 (s), 2980 (s), 2980 (sh), 1640 (m), 1480 (m), 1400 (w), 1330 (w), 1260 (w), 1220 (w), 1140 (w), 1120 (w), 1060 (w), 1020 (w), 1010 (w), 910 (w), 890 (w), 760 (w).

(s represents a strong absorption; m, a medium absorption; w, a weak absorption, and sh, shoulder. These abbreviations have the same meanings hereinafter)

EXAMPLE 12

2.01 g of 6,7-dihydroxy-2,5,5,8a-tetramethyl-1,2,3,4,4a,5,6,7,8,8a-decahydronaphthalene-1-spiro-2'-(6α,7'-diformyl-4'-hydroxy-2',3'-dihydrobenzofuran) was dissolved in 50 ml of ethanol, and 1.45 g of malononitrile and one drop of piperidine as a catalyst were added thereto. The mixture was stirred at 50° C. for 30 minutes. After the reaction, the reaction mixture was concentrated to a volume of 10 ml under reduced pressure, and allowed to cool. The crystals which precipitated were collected by filtration, and washed with ice cold ethanol. The resulting crude crystals were dissolved in 50 ml of a 1 N aqueous solution of sodium hydroxide, and treated with activated carbon. With ice cooling, hydrochloric acid was added to render the solution acidic (pH 2 to 3). The crystals which precipitated were collected by filtration, thoroughly washed with water, and dried. Thus, 1.02 g of 6,7-dihydroxy-2,5,5,8a-tetramethyl-1,2,3,4,4a,5,6,7,8,8a-decahydronaphthalene-1-spiro-2'-[6',7'-di-(2,2-dicyanovinyl)-4'-hydroxy-2',3'-dihydrobenzofuran] as yellow amorphous crystals was obtained. Production of this compound was confirmed by the following physicochemical properties.

(1) Melting Point: Gradual decomposition at about 230° C., and no definite melting point observed.

(2) Elemental Analysis Values for $C_{29}H_{30}O_4N_4$: Calculated (%): C, 69.86; H, 6.07; N, 11.24. Found (%): C, 69.58; H, 6.32; N, 11.09.

(3) Infrared Absorption Spectral (IR) Analysis The product had the following $\nu_{max}(cm^{-1})$.

3450 (s), 2980 (s), 2900 (sh), 2210 (s), 1720 (w), 1660 (sh), 1640 (s), 1580 (sh), 1520 (w), 1470 (m), 1400 (m), 1380 (m), 1360 (m), 1340 (m), 1260 (m), 1200 (w), 1110 (w), 1050 (m), 1020 (w), 1000 (w), 980 (w), 960 (w), 940 (w), 900 (w), 840 (w), 760 (w) using the KBr tablet method.

EXAMPLE 13

2.01 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) was dissolved in 40 ml of ethanol, and 3 ml of ethyl cyanoacetate was added thereto. Further, three drops of piperidine as a catalyst were added thereto, and the mixture was stirred at 60° C. for 2 hours. After the reaction, the reaction mixture was concentrated to dryness under reduced pressure. The residue was washed with a small amount of dilute hydrochloric acid (1 N), washed with water, and dried to form crude crystals. The crude crystals were dissolved in 50 ml of a mixture of methanol and water (1:1 by volume), and treated with activated carbon. An equal quantity by volume of water was further added to precipitate crystals. The crystals were collected by filtration, washed with water, and dried. Thus, 1.89 g of 6,7-dihydroxy-2,5,5,8a-tetramethyl-1,2,3,4,4a,5,6,7,8a-decahydronaphthalene-1-spiro-2'-[6',7'-di-(2-cyano-2-ethoxycarbonylvinyl)-4'-hydroxy-2',3'-dihydrobenzofuran] are obtained as light amorphous crystals. Production of this compound was confirmed by the following physicochemical properties.

(1) Melting Point: 161.0°–167.0° C.

(2) Elemental Analysis Values for $C_{33}H_{40}O_8N_2$: Calculated (%): C, 66.87; H, 6.80; N 4.73. Found (%): C, 66.63; H, 7.02; N 4.51.

(3) Infrared Adsorption Spectral (IR) Analysis The product had the following $\nu_{max}(cm^{-1})$ using the KBr tablet method.

3450 (s), 2970 (sh), 2950 (m), 2900 (sh), 2240 (w), 1740 (s), 1630 (s), 1470 (s), 1460 (sh), 1400 (w), 1300 (w), 1250 (s), 1100 (m), 1050 (m), 1030 (m), 1020 (sh), 970 (w), 950 (sh), 940 (w), 900 (sh), 890 (w), 860 (w).

EXAMPLE 14

3.00 mg of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2 ',3'-dihydrobenzofuran) was dissolved in 20 ml of pyridine, and 10.0 g of cyanoactetic acid and 1 drop of piperidine as a catalyst were added thereto. The mixture was stirred at 50° C. for 5 hours. After the reaction, the reaction mixture was concentrated to dryness. 50 ml of water was added to the residue to obtain crystals of the residue. The crystals were collected by filtration, washed with water, then with dilute hydrochloric acid (1 N), and again with water. The crude crystals were dissolved in 100 ml of a 10% aqueous solution of sodium bicarbonate. The insoluble matter was separated by filtration, and the filtrate was acidified to pH 2 to 3 with hydrochloric acid with ice cooling. The crystals which precipitated were collected by filtration, washed with water, and dried to afford 1.1 g of 6,7-dihydroxy-2,5,5,8a-tetramethyl-1,2,3,4,4a5,6,7,8,8a-decahydronaphthalene-1-spiro-2'-[6',7'-di-(2-cyano-2-carboxyvinyl)-4'-hydroxy-2',3'-dihydrobenzofuran] as light yellow amorphous crystals. Production of this compound was confirmed by the following physicochemical properties.

(1) Melting Point: 217°–223° C.

(2) $[\alpha]_D^{20} = -23.2°$ (C=0.8, methanol)

(3) Elemental Analysis Values for $C_{29}H_{32}N_2O_8$: Calculated (%): C, 64.91; H, 6.01; N, 5.22. Found (%): C, 64.63; H, 6.25; N, 5.01.

(4) Infrared Absorption Spectral (IR) Analysis

The product had the following $\nu_{max}(cm^{-1})$ using the KBr tablet method.

3450 (s), 2950 (m), 2870 (sh), 2240 (w), 1710 (s), 1660 (m), 1610 (s), 1580 (m), 1460 (m), 1440 (m), 1400 (m), 1300 (m), 1250 (m), 1200 (sh), 1120 (w), 1100 (w), 1040 (w), 880 (w).

EXAMPLE 15

1.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) was dissolved in 10 ml of pyridine, and 1.0 g of malonic acid and, as a catalyst, 3 drops of piperidine were added thereto. The mixture was heated under reflux for 4 hours. After the reaction, 200 ml of water was added to the reaction mixture, and the mixture was acidified to pH 2 to 3 with hydrochloric acid and allowed to cool. The precipitated tarry material was collected, washed with water, dissolved in 100 ml of methanol, treated with activated carbon, and concentrated to dryness under reduced pressure. The residue was recrystallized from a mixture of methanol and water (1:1 by volume) to afford 0.58 g of 6,7-dihydroxy-2,5,5,8a-tetramethyl-1,2,3,4,4a,5,6,7,8,8a-decahydronaphthalene-1-spiro-2'-[6',7'-di-(2-carboxyvinyl)-4'-hydroxy-2',3'-dihydrobenzofuran] an light brown amorphous crystals. Production of this compound was confirmed by the following physicochemical properties.

(1) Melting Point: 190°–196° C.

(2) Elemental Analysis Values for $C_{27}H_{34}O_8$: Calculated (%): C, 66.65; H, 7.04. Found (%): C, 66.36; H, 7.31.

(3) Infrared Absorption Spectral (IR) Analysis The product has the following $\nu_{max}(cm^{-1})$ using the KBr tablet method.

3450 (s), 2970 (m), 2950 (m), 2890 (sh), 1690 (s), 1620 (s), 1470 (s), 1390 (s), 1350 (m), 1330 (m), 1290 (w), 1260 (m), 1200 (w), 1120 (w), 1070 (w), 1050 (m), 960 (w), 950 (m).

EXAMPLE 16

1.0 g of sodium borohydride was dissolved in 20 ml of a 0.1 N aqueous solution of sodium hydroxide. A solution of 0.9 g of 4,6-dihydroxy-8-oxo-2,3,6,8-tetrahydrofuro[3,4-g]benzofuran-2-spiro-1'-(6',7'-dihydroxy-2',5',5',8'a-tetramethyl-1',2',3',4',4'a,5',6',7',8',8'a-decahydronaphthalene) in 10 ml of a 1% aqueous solution of sodium hydroxide. The mixed solution was stirred at 60° C. for 18 hours, cooled with ice to about 2° to 5° C., and acidified with hydrochloric acid (1 N). The solution was concentrated to dryness under reduced pressure, and the residue was dissolved in 50 ml of ethyl acetate. The insoluble matter was separated by filtration. The filtrate was washed with water, and dried over anhydrous sodium sulfate. The sodium sulfate was removed by filtration, and the residue was concentrated to dryness under reduced pressure. The residue was recrystallized from 10 ml of a mixture of methanol and water (1:1 by volume) to afford 0.28 g of 6,7-dihydroxy-2,5,5,8a-tetramethyl-1,2,3,4,4a,5,6,7,8,8a-decahydronaphthalene-1-spiro-2'-(7'-carboxy-6'-hydroxymethyl-4'-hydroxy-2',3'-dihydrobenzofuran) as colorless amorphous crystals. Production of this compound was confirmed by the following physicochemical properties.

(1) Melting Point: 212°–216° C.

(2) Elemental Analysis Values for $C_{23}H_{32}O_7$: Calculated (%): C, 65.71; H, 7.62. Found (%): C, 65.74; H, 7.47.

(3) Infrared Absorption Spectral (IR) Analysis The product had the following $\nu_{max}(cm^{-1})$ using the KBr tablet method.

3450 (s), 2950 (sh), 2920 (m), 2900 (sh), 1740 (s), 1620 (m), 1475 (s), 1400 (w), 1360 (w), 1340 (m), 1260 (w), 1140 (w), 1080 (m), 1050 (w), 1030 (w), 960 (sh), 950 (m), 780 (w).

EXAMPLE 17

4.02 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) was dissolved by heating (about 60° to 70° C.) in 100 ml of benzene. Then, 10 ml of diethyl malonate and as a catalyst, one drop of piperidine was added thereto. Water was removed by an azeotropic distillation. The distillation was performed for 4 hours, and when almost a theoretical amount of water was removed, the mixture was concentrated under reduced pressure. The remaining tarry material was washed with diethyl ether, and the ether-insoluble portion was collected by filtration, dried and recrystallized from a mixture of diethyl ether and water (1:2 by volume). Thus, 1.32 g of 6,7-dihydroxy-2,5,5,8a-tetramethyl-1,2,3,4,4a,5,6,7,8,8a-decahydronaphthalene-1-spiro-2'-[6',7'-di-(2,2-diethoxycarbonylvinyl)-4'-hydroxy-2',3'-dihydrobenzofuran] was obtained as colorless amorphous crystals. Production of this compound was confirmed by the following physicochemical properties.

(1) Melting Point: 138°–142° C.

(2) Elemental Analysis Values for $C_{37}H_{50}O_{12}$: Calculated (%): C, 64.70; H, 7.34. Found (%): C, 64.43; H, 7.59.

(3) Infrared Absorption Spectral (IR) Analysis The compound has the following $\nu_{max}(cm^{-1})$ using the KBr tablet method.

3450 (s), 2980 (sh), 2950 (s), 2900 (s), 2880 (sh), 1730 (s), 1680 (m), 1630 (sh), 1600 (s), 1470 (m), 1440 (m), 1400 (m), 1320 (m), 1250 (s), 1120 (w), 1100 (w), 1080 (w), 1050 (w), 1020 (w), 970 (w), 950 (w), 890 (w), 760 (m).

EXAMPLE 18

1.0 g of sodium borohydride was dissolved in 50 ml of a 1 N aqueous solution of sodium hydroxide, and at room temperature, a solution of 4.02 g of 6,7-dihdyroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) in 20 ml of a 1 N aqueous solution of sodium hydroxide was added thereto. The mixed solution was stirred for 3 hours. After the reaction, the reaction mixture was acidified to pH 2 to 3 with hydrochloric acid with ice cooling (about 2° to 5° C.). The crystals which precipitated were collected by filtration, washed with water, and dried. The crude crystals were recrystallized from 50 ml of a mixture of methanol and water (1:5 by volume) to afford 2.51 g of 6,7-dihydroxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) as light brown amorphous crystals. Production of this compound was confirmed by the following physicochemical properties.

(1) Melting Point: Gradually decomposed at about 270° C., and showed no definite melting point.

(2) Elemental Analysis Values for $C_{23}H_{34}O_6$: Calculated (%): C, 67,95; H, 8.43. Found (%): C, 67.71; H, 8.66.

(3) Infrared Absorption Spectral (IR) Analysis The product has the following $\nu_{max}(cm^{-1})$ using the KBr tablet method.

3450 (s), 2920 (m), 2880 (m), 1620 (m), 1600 (sh), 1440 (m), 1390 (w), 1320 (w), 1260 (m), 1200 (w), 1100 (m), 1040 (w), 1000 (w), 980 (w), 940 (w), 830 (w).

EXAMPLE 19

1.00 g of 6,7-dihydroxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) was dissolved in 50 ml of methanol. The solution was added dropwise to 20 ml of a freshly prepared diethyl ether solution containing 1.0 g of diazomethane through a dropping funnel at room temperature. The mixture was stirred at room temperature for 2 hours, and then cooled with ice (about 2° to 5° C.). Hydrogen chloride gas was bubbled into the mixture to decompose the excess diazomethane. Then, 100 ml of water was added thereto, and the mixture was concentrated to dryness under reduced pressure. To the residue was added 10 ml of a 0.1 N aqueous solution of sodium hydroxide, and the insoluble portion was collected by filtration, washed with water and dried. Thus, 0.87 g of 6,7-dihydroxy-2,5,5,8a-tetramethyl-1,2,3,4,4a,5,6,7,8,8a-decahydronaphthalene-1-spiro-2'-(6',7'-dihydroxymethyl-4'-methoxy-2',3'-dihydrobenzofuran) was obtained as colorless amorphous crystals. Production of this compound was confirmed by the following physicochemical properties.

(1) Melting Point: 107°–115° C.

(2) Elemental Analysis Values for $C_{24}H_{36}O_6$: Calculated (%): C, 68.54; H, 8.63. Found (%): C, 68.31; H, 8.90.

(3) Infrared Absorption Spectral (IR) Analysis The product has the following $\nu_{max}(cm^{-1})$ using the KBr tablet method.

3320 (s), 2920 (m), 2880 (m), 1720 (w), 1620 (m), 1600 (s), 1500 (sh), 1450 (m), 1420 (m), 1390 (w), 1320 (m), 1230 (m), 1200 (w), 1120 (s), 1040 (m), 1000 (m), 940 (w), 820 (w).

EXAMPLE 20

2.00 g of 6,7-dihydroxy-2,5,5,8a-tetramethyl-1,2,3,4,4a,5,6,7,8,8a-decahydronaphthalene-1-spiro-2'-(7'-carboxy-6'-hydroxymethyl-4'-hydroxy-2',3'-dihydrobenzofuran) was dissolved in 50 ml of ethyl acetate, and 10 mg of p-toluenesulfonic acid was added thereto. The mixture was heated under reflux. After the reaction, the reaction mixture was cooled to room temperature, washed with 10 ml of a 1 N aqueous solution of sodium hydroxide, thoroughly washed with water, and dried over anhydrous sodium sulfate. The sodium sulfate was separated by filtration, and the residue was concentrated to dryness under reduced pressure. Thus, 1.45 g of 4-hydroxy-8-oxo-2,3,6,8-tetrahydrofuro[3,4-g]benzofuran-2-spiro-1'-(6',7'-dihydroxy-2',5',5',8'a-tetramethyl-1',2',3',4',4'a,5',6',7',8',8'a-decahydronaphthalene) was obtained as colorless amorphous crystals. Production of this compound was confirmed from the following physicochemical properties.

(1) Melting Point: 187°–193° C.

(2) Elemental Analysis Values for $C_{23}H_{30}O_6$: Calculated (%): C, 68.63; H, 7.51. Found (%): C, 68.47; H, 7.70.

(3) Infrared Absorption Spectral (IR) Analysis The product had the following $\nu_{max}(cm^{-1})$ using the KBr tablet method.

3280 (s), 2950 (m), 2890 (m), 1730 (s), 1610 (m), 1460 (s), 1330 (s), 1240 (w), 1130 (w), 1080 (m), 1040 (w), 1000 (w), 940 (m), 750 (m).

EXAMPLE 21

100 mg of 6,7-dihydroxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) was dissolved in 2 ml of dry pyridine, and 1 ml of acetic anhydride was added thereto. The mixture was allowed to stand overnight at room temperature. Ice water was added to the reaction mixture. The precipitate was collected by filtration, and recrystallized from a mixture of ethyl acetate and n-hexane by adding n-hexane portionwise to the ethyl acetate solution until crystals precipitated. Thus, 105 mg of 7-acetyloxy-6-hydroxy-2,5,5,8a-tetramethyl-1,2,3,4,4a,5,6,7,8,8a-decahydronaphthalene-1-spiro-2'-(6',7'-diacetyloxymethyl-4'-acetyloxy-2',3'-dihydrobenzofuran) was obtained as white crystals. Production of this compound was confirmed by the following physicochemical properties.

(1) Melting Point: 78°–83° C.

(2) Elemental Analysis Values for $C_{31}H_{42}O_{10}$: Calculated (%): C, 64.79; H, 7.37. Found (%): C, 64.51; H, 7.19.

(3) Infrared Absorption Spectral (IR) Analysis The product had the following $\nu_{max}(cm^{-1})$ using the KBr tablet method.

3430 (w), 2900 (m), 2860 (sh), 1763 (sh), 1730 (s), 1715 (sh), 1620 (m), 1600 (m), 1465 (sh), 1447 (sh), 1430 (s), 1378 sh), 1364 (s), 1302 (m), 1250 (sh), 1220 (s), 1195 (s), 1160 (sh), 1126 (m), 1096 (s), 1020 (s), 1000 (sh), 980 (m), 950 (m), 915 (sh), 895 (sh), 865 (sh), 830 (sh), 810 (sh), 763 (w), 690 (sh), 592 (w).

EXAMPLE 22

100 mg of 6,7-dihydorxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) was dissolved in 2 ml of dry pyridine, and 1 ml of acetic anhydride was added thereto. The mixture was heated at 100° C. for 2 hours. Ice water was added to the reaction mixture. The resulting precipitate was collected by filtration, and recrystallized from a mixture of ethyl acetate and n-hexane by adding portionwise n-hexane to the ethyl acetate solution until crystals precipitated to afford 115 mg of 6,7-diacetyloxy-2,5,5,8a-tetramethyl-1,2,3,4,4a,5,6,7,8,8a-decahydronaphthalene-1-spiro-2'-(6',7'-acetyloxymethyl-4'-acetyloxy-2',3'-dihydrobenzofuran) as white crystals. Production of this compound was confirmed by the following physicochemical properties.

(1) Melting Point: 76°–80° C.

(2) Elemental Analysis Values for $C_{33}H_{44}O_{11}$: Calculated (%): C, 64.27; H, 7.19. Found (%): C, 64.12; H, 7.03.

(3) Infrared Absorption Spectral (IR) Analysis The product had the following $\nu_{max}(cm^{-1})$ using the KBr tablet method.

2920 (m), 2880 (sh), 1760 (sh), 1750 (sh), 1730 (s), 1624 (sh), 1603 (m), 1473 (sh), 1457 (sh), 1447 (sh), 1428 (s), 1376 (sh), 1363 (s), 1300 (s), 1260 (sh), 1220 (s), 1195 (s), 1150 (sh), 1125 (w), 1095 (s), 1035 (sh), 1020 (s), 980 (sh), 953 (s), 915 (m), 895 (sh), 870 (sh), 820 (w), 765 (w), 715 (w), 686 (w), 657 (w), 618 (sh), 596 (m), 583 (m).

EXAMPLE 23

100 mg of 7-acetyloxy-6-hydroxy-2,5,5,8a-tetramethyl-1,2,3,4,4a,5,6,7,8,8a-decahydronaphthalene-1-spiro-2'-(6',7'-diacetyloxymethyl-4'-acetyloxy-2',3'-dihydrobenzofuran) was dissolved in 5 ml of aceotne, and with ice cooling, 0.1 ml of Jones reagent was added dropwise thereto. The mixture was stirred for 1 hour. Isopropanol was added dropwise to the reaction mixture to decompose the excess Jones reagent. Then, ice water was added thereto, and the mixture was extracted with ethyl acetate. The organic layer was washed with water, and the solvent was distilled off. The residue was recrystallized from a mixture of acetone and n-hexane by adding n-hexane portionwise to the acetone solution until crystals precipitated to afford 72 mg of 7-acetyloxy-6-oxo-2,5,5,8a-tetramethyl-1,2,3,4,4a,5,6,7,8-,8a-decahydronaphthalene)-1-spiro-2'-(6',7'-diacetyloxymethyl-4'-acetyloxy-2',3'-dihydrobenzofuran) as white crystals. Production of this compound was confirmed by the following physicochemical properties.

(1) Melting Point: 140°-143° C.

(2) Elemental Analysis for $C_{31}H_{40}O_{10}$ Calculated (%): C, 65.02; H, 7.04. Found (%): C, 65.17; H, 7.13.

(3) Infrared Absorption Spectral (IR) Analysis The product had the following $\nu_{max}(cm^{-1})$ using the KBr tablet method.

2900 (m), 2880 (sh), 1766 (sh), 1750 (s), 1720 (s), 1628 (m), 1600 (m), 1456 (s), 1427 (s), 1380 (sh), 1363 (s), 1340 (sh), 1300 (s), 1265 (sh), 1220 (s), 1185 (s), 1120 (m), 1083 (s), 1070 (sh), 1030 (s), 1013 (sh), 1000 (sh), 970 (m), 950 (s), 936 (sh), 926 (sh), 905 (m), 895 (m), 870 (m), 854 (sh), 827 (w), 780 (w), 766 (w), 738 (w), 712 (w), 666 (w), 610 (w), 588 (w).

EXAMPLE 24

100 mg of 4-hydroxy-8-oxo-2,3,6,8-tetrahydrofuro[3,4-g]benzofuran-2-spiro-1'-(6',7'-dihydroxy-2',5',5',8'a-tetramethyl-1',2',3',4',4'a,5',6',7',8',8'a-decahydronaphthalene) was dissolved in 2 ml of dry acetone, and 1 ml of 2,2-dimethoxypropane and then 5 mg of anhydrous p-toluenesulfonic acid were added thereto. The mixture was stirred at room temperature for 2 hours. Water was added to the reaction solution, and the mixture was extracted with ethyl acetate. The organic layer was washed with a saturated aqueous solution of sodium bicarbonate and then with water. The solvent was evaporated off, and the residue was recrystallized from a mixture of ethyl acetate and n-hexane to afford 83 mg of 4-hydroxy-8-oxo-2,3,6,8-tetrahydro-furo[3,4-g]benzofuran-2-spiro-1'-(6',7'-isopropylidenedioxy-2',5',5',8'a-tetramethyl-1',2',3',4',4'a,5',6',7',8',8'a-decahydronaphthalene) as white crystals. Production of this compound was confirmed by the following physicochemical properties.

(1) Melting Point: 142°-150° C.

(2) Elemental Analysis Values for $C_{26}H_{33}O_6$: Calculated (%): C, 70.73; H, 7.53. Found (%): C, 70.51; H, 7.38.

(3) Infrared Absorption Spectral (IR) Analysis The product had the following $\nu_{max}(cm^{-1})$ using the KBr tablet method.

3280 (w), 2920 (m), 2880 (sh), 1760 (sh), 1733 (s), 1620 (sh), 1608 (m), 1463 (s), 1387 (sh), 1368 (m), 1354 (s), 1330 (s), 1300 (sh), 1255 (sh), 1238 (m), 1216 (s), 1178 (w), 1153 (w), 1124 (w), 1106 (w), 1080 (m), 1060 (m), 1043 (s), 1016 (m), 1005 (sh), 985 (sh), 950 (m), 923 (w), 895 (w), 870 (sh), 858 (m), 784 (sh), 768 (sh), 753 (m).

EXAMPLE 25

100 mg of 6,7-dihydroxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) was dissolved in 2 ml of dry acetone, and 1 ml of 2,2-dimethoxypropane and 5 mg of anhydrous p-toluenesulfonic acid were added thereto. The mixture was stirred for 30 minutes at room temperature. Ice water was added to the reaction solution, and the mixture extracted with ethyl acetate. The organic layer was washed with a saturated aqueous solution of sodium bicarbonate and then with water, and the solvent was distilled off. The residue was purified by silica gel column chromatography, and recrystallized from a mixture of ethyl acetate and n-hexane by adding n-hexane portionwise to the ethyl acetate solution until crystals precipitated to afford 21 mg of 6,7-isopropylidenedioxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) was white crystals. Production of this compound was confirmed by the following physicochemical properties.

(1) Melting Point: Gradually decomposed to about 200° C. with coloration, and no definite melting point shown.

(2) Elemental Analysis Values for $C_{26}H_{38}O_6$ Calculated (%): C, 69.93; H, 8.58. Found (%): C, 69.71; H, 8.39.

(3) Infrared Absorption Spectral (IR) Analysis The product had the following $\nu_{max}(cm^{-1})$ using the KBr tablet method.

3360 (m), 3040 (m), 2920 (m), 2880 (sh), 1735 (w), 1700 (w), 1618 (m), 1458 (sh), 1440 (s), 1386 (sh), 1368 (s), 1346 (m), 1313 (m), 1253 (m), 1237 (m), 1215 (m), 1180 (w), 1150 (w), 1106 (s), 1083 (m), 1052 (sh), 1047 (s), 1026 (m), 1000 (s), 974 (s), 952 (m), 920 (w), 895 (w), 870 (sh), 857 (m), 837 (m), 785 (w), 765 (sh), 700 (w), 670 (w).

EXAMPLE 26

100 mg of 4-hydroxy-8-oxo-2,3,6,8-tetrahydrofuro[3,4-g]benzofuran-2-spiro-1'-(6',7'-isopropylideneoxy-2',5',5',8'a-tetramethyl-1',2',3',4',4'a,5',6',7',8',8'a-decahydronaphthalene was dissolved in 5 ml of dry diethyl ether, and with ice cooling, 5 mg of lithium aluminum hydride was added. The mixture was stirred for 1 hour. Ice water was added to the reaction solution, and the solution was rendered weakly acidic (pH 3 to 5) with 1 N hydrochloric acid, and then extracted with ethyl acetate. The organic layer was washed with water, and the solvent was distilled off. The residue was recrystallized from a mixture of ethyl acetate and n-hexane by adding n-hexane portionwise to the ethyl acetate solution until crystals precipitated to afford 75 mg of 6,7-isopropylidenedioxy-2,5,5,8a-tetramethyl-1,2,3,4,4a,5,6,7,8,8a-decahydronaphthalene-1-spiro-2'-(6',7'-dihydroxymethyl-4'-hydroxy-2',3'-dihydrobenzofuran) as white crystals. The physico-chemical properties of the resulting compound agreed with those of the compound obtained in Example 25.

REFERENCE EXAMPLE 1

| Compound No. 1 of the invention | 500 mg |
| Glucose | 250 mg |
| Distilled Water for Injection | to make the total amount 5 ml |

The disodium salt [III] of the present Compound No. 1 and glucose were dissolved in distilled water for injection. The solution was poured into a 5 ml ampoule. The air was purged with nitrogen, and the ampoule was heated at 121° C. for 15 minutes to sterilize the solution to obtain an injectable preparation.

REFERENCE EXAMPLE 2

| | |
|---|---|
| Compound No. 67 of the Invention | 500 mg |
| Sodium Sulfite | 5 mg |
| Distilled Water for Injection | to make the total amount 5 ml |

In a manner similar to Reference Example 1, an injectable preparation was prepared.

REFERENCE EXAMPLE 3

| | |
|---|---|
| Compound No. 6 of the Invention | 500 mg |
| Sodium Sulfite | 5 mg |
| Distilled Water for Injection | to make the total amount 5 ml |

In a manner similar to Reference Example 1, an injectable preparation was prepared.

REFERENCE EXAMPLE 4

| | |
|---|---|
| Compound No. 6 of the Invention | 750 mg |
| Semi-synthetic Glyceride Base | to make the total amount 2000 mg |

Compound No. 6 of the invention was added to the semi-synthetic glyceride base, and they were mixed and suspended at 50° C. The mixture was cast into a mold, and allowed to cool naturally. The product was removed, and thus, a suppository was obtained.

REFERENCE EXAMPLE 5

| | |
|---|---|
| Compound No. 2 of the Invention | 750 mg |
| Vitamin E | 90 mg |
| Semi-synthetic Glyceride Base | to make the total amount 2000 mg |

In a manner similar to Reference Example 4, a suppository was obtained.

REFERENCE EXAMPLE 6

| | |
|---|---|
| Compound No. 67 of the Invention | 150 g |
| Avicel (trademark for a product of Asahi Kasei Kabushiki Kaisha) | 40 g |
| Corn Starch | 30 g |
| Magnesium Stearate | 2 g |
| TC-5 (trademark for hydroxypropylmethyl cellulose, produced by Shinetsu Chemical Industry Co., Ltd.) | 10 g |
| Macrogol 6000 (polyethylene grycol having a molecular weight of about 6000 produced by Shinetsu Chemical Industry Co., Ltd.) | 3 g |
| Castor Oil | 40 g |
| Methanol | 40 g |

Compound No. 67 the Avicel, the corn starch and the magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, Macrogol-6000, castor oil and methanol to produce film-coated tablets.

REFERENCE EXAMPLE 7

| | |
|---|---|
| Compound No. 6 of the Invention | 100 g |
| Avicel | 40 g |
| Corn Starch | 30 g |
| Magnesium Stearate | 2 g |
| Methyl Acrylate/Methacrylic Acid Copolymer | 5.7 g |
| Triacetin | 0.6 g |
| Ethanol | 50.4 g |

Compound No. 6, the Avicel, the corn starch and the magnesium stearate were mixed and ground, and tableted using a pounder for sugar coating (R 10 mm). The resulting tablets were coated with a film coating agent composed of the methyl acrylate/methacrylic acid copolymer, the triacetin and the ethanol to form enteric-coated tablets.

REFERENCE EXAMPLE 8

| | |
|---|---|
| Compound No. 6 of the Invention | 150.0 g |
| Citric Acid | 1.0 g |
| Lactose | 33.5 g |
| Dicalcium Phosphate | 70.0 g |
| Plon F-68 (Plulonic F-68, nonionic surface active agent) | 30.0 g |
| Sodium Laurylsulfate | 15.0 g |
| Polyvinyl Pyrrolidone | 15.0 g |
| Polyethylene Glycol (Carbowax 1500) | 4.5 g |
| Polyethylene Glycol (Carbowax 6000) | 45.0 g |
| Corn Starch | 30.0 g |
| Dry Sodium Laurylsulfate | 3.0 g |
| Dry Magnesium Stearate | 3.0 g |
| Ethanol | Suitable amount |

Compound No. 6, the citric acid, the lactose, the dicalcium phosphate, the Plon F-68 and the sodium laurylsulfate were mixed.

The mixture was sieved using a No. 60 screen, and wet-granulated with an alcoholic solution composed of the polyvinyl pyrrolidone, the Carbowax 1500 and the Carbowax 6000. Ethanol was optionally added to convert the powder into a paste-like mass. The corn starch was added, and mixing was continued until uniform particles formed. The particles were passed through a No. 10 screen, placed in a tray, and dried in an oven at 100° C. for 12 to 14 hours. The dried particles were sieved through a No. 16 screen, and mixed with the dry sodium laurylsulfate and the dry magnesium stearate. The mixture was compressed to the desired shape using a tableting machine.

The corn portions thus obtained were treated with a varnish, and talc was sprayed thereon to prevent moisture absorption. The core portions were coated with a primer layer and then with a varnish the required number of times for peroral administration. To round and smoothen the tablets completely, tae primer and smooth coating were further applied, and a colored coating was applied until the desired color was obtained. After drying, the coated tablets were polished to form tablets having a uniform gloss.

While the invention has been described in detail and with reference to specific embodiments thereof, it will be apparent to one skilled in the art that various changes and modifications can be made therein without departing from the spirit and scope thereof.

What is claimed is:

1. A sesquiterpene derivative expressed by the general formula (I):

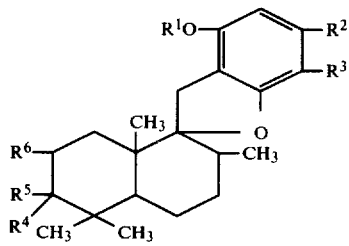

wherein $R^1$ represents a hydrogen atom, a lower alkyl group or a lower alkanoyl group; $R^2$ and $R^3$, which may be the same or different, each represents a formyl group, a hydroxymethyl group, a hydroxyl group, a carboxyl group, a lower alkanoyloxymethyl group, or a group having the formula $-CH=CR^7R^8$ in which $R^7$ and $R^8$, which may be the same or different, each represents a hydrogen atom, a cyano group, a lower alkoxycarbonyl group or a carboxyl group, or $R^2$ and $R^3$ may combine and form a lactone ring of the formula

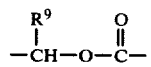

in which $R^9$ represents a hydrogen atom or a hydroxyl group; $R^4$ and $R^6$, which may be the same or different, each represents a hydroxyl group or a lower alkanoyloxy group; $R^5$ represents a hydrogen atom; $R^4$ and $R^5$ may together form an oxo group; and $R^4$ and $R^6$ may combine to form a lower alkylidenedioxy group; or the pharmaceutically acceptable salts thereof.

2. A compound of the formula (Ia):

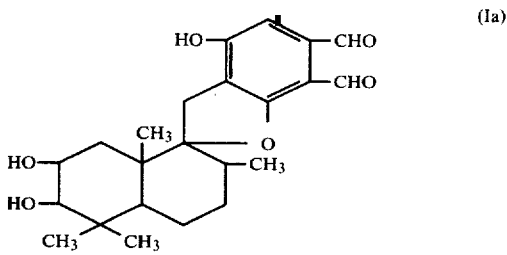

or the pharmaceutically acceptable salts thereof, according to claim 1.

3. Disodium 6,7-dihydroxy-2,5,5,8a-tetramethyl-1,2,3,4,4a,5,6,7,8,8a-decahydronaphthalene-1-spiro-2'-(7'-carboxylate-6'-formyl-4'-oxide-2',3'-dihydrobenzofuran)

4. A pharmaceutical composition having anticomplementary activity in animals comprising a therapeutically effective amount of the sesquiterpene derivative or the pharmaceutically acceptable salt thereof according to claim 1 and a pharmaceutically acceptable carrier.

5. The composition according to claim 4, wherein the amount of the sesquiterpene derivative or the pharmaceutically acceptable salt thereof is about 1 to about 70% by weight based on the entire weight of the pharmaceutical composition.

6. A method for treating nephritis, which comprises administering a pharmaceutical composition containing the sesquiterpene derivative or the pharmaceutically acceptable salt thereof according to claim 1 and a pharmaceutically acceptable carrier to a nephritic patient in a daily dose of about 0.5 to about 20 mg/kg of body weight per day based on the sesquiterpene derivative.

* * * * *